United States Patent
Moriyama et al.

(10) Patent No.: US 9,682,961 B2
(45) Date of Patent: Jun. 20, 2017

(54) QUINAZOLINE DERIVATIVE

(71) Applicants: CARNA BIOSCIENCES, INC., Kobe-shi, Hyogo (JP); NATIONAL CANCER CENTER, Tokyo (JP)

(72) Inventors: Hideki Moriyama, Kobe (JP); Masaaki Sawa, Ibaraki (JP); Yuko Uno, Kobe (JP); Shigeki Kashimoto, Osaka (JP); Tesshi Yamada, Tokyo (JP)

(73) Assignees: CARNA BIOSCIENCES, INC., Kobe-Shi (JP); NATIONAL CANCER CENTER, Tokyo (JP)

( * ) Notice: Subject to any disclaimer, the term of this patent is extended or adjusted under 35 U.S.C. 154(b) by 0 days.

(21) Appl. No.: 14/890,868

(22) PCT Filed: Dec. 5, 2014

(86) PCT No.: PCT/JP2014/082300
§ 371 (c)(1),
(2) Date: Nov. 12, 2015

(87) PCT Pub. No.: WO2015/083833
PCT Pub. Date: Jun. 11, 2015

(65) Prior Publication Data
US 2016/0264555 A1  Sep. 15, 2016

(30) Foreign Application Priority Data

Dec. 6, 2013 (JP) ................. 2013-253222

(51) Int. Cl.
| C07D 403/12 | (2006.01) |
| C07D 413/12 | (2006.01) |
| C07D 417/12 | (2006.01) |
| C07D 401/12 | (2006.01) |

(52) U.S. Cl.
CPC ......... *C07D 403/12* (2013.01); *C07D 401/12* (2013.01); *C07D 413/12* (2013.01); *C07D 417/12* (2013.01)

(58) Field of Classification Search
CPC .................................................. C07D 403/12
See application file for complete search history.

(56) References Cited

U.S. PATENT DOCUMENTS

| 2010/0056506 A1 | 3/2010 | Huang et al. |
| 2010/0311965 A1 | 12/2010 | Sawa et al. |

FOREIGN PATENT DOCUMENTS

| JP | 2009-535393 A | 10/2009 |
| KR | 10-2013-0084474 A | 7/2013 |
| WO | WO 2007/117607 A3 | 10/2007 |
| WO | WO 2009/084695 A1 | 7/2009 |
| WO | WO 2012/044090 A2 | 4/2012 |
| WO | WO 2012/088712 A1 | 7/2012 |
| WO | WO 2012/136492 A1 | 10/2012 |

OTHER PUBLICATIONS

International Search Report, issued in PCT/JP2014/082300, dated Jan. 13, 2015.
International Preliminary Report on Patentability and English translation of the Written Opinion of the International Searching Authority issued in the International Application No. PCT/JP2014/082300 on Jun. 16, 2016.
Clevers et al., "Wnt/•-Catenin Signaling and Disease", Cell, vol. 149, Jun. 8, 2012, pp. 1192-1205.
Dean et al., "Tumour Stem Cells and Drug Resistance", Nature Reviews Cancer, vol. 5, Apr. 2005, pp. 275-284.
Holland et al., "Wnt signaling in stem and cancer stem cells", Current Opinion in Cell Biology, vol. 25, 2013 (Available online Jan. 21, 2013), pp. 254-264.
Li et al., "Beyond tumorigenesis: cancer stem cells in metastasis", Cell Research, vol. 17, 2007 (published online Dec. 19, 2006), pp. 3-14.
Logan et al., "The Wnt Signaling Pathway in Development and Disease", Annu. Rev. Cell Dev. Biol., vol. 20, 2004 (published online Jul. 2, 2004), pp. 781-810.
Reya et al., "Wnt signalling in stem cells and cancer", Nature, vol. 434, Apr. 14, 2005, pp. 843-850.
European Patent Office Communication and extended search report issued in the corresponding European Patent Application No. 14868296.6 on Apr. 21, 2017.

*Primary Examiner* — Paul V Ward
(74) *Attorney, Agent, or Firm* — Birch, Stewart, Kolasch & Birch, LLP

(57) ABSTRACT

The present invention provides a quinazoline derivative represented by the following formula (I):

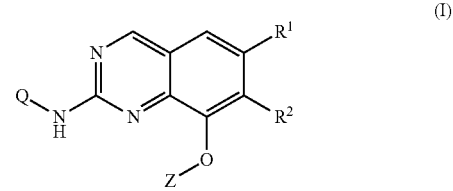

wherein $R^1$ and $R^2$ represent a hydrogen atom, a halogen atom, or a lower alkyl group optionally having a substituent; Z represents a cycloalkyl group having a substituent or a cycloalkenyl group having a substituent; and Q represents a bicyclic heteroaryl group optionally having a substituent, or a pharmaceutically acceptable salt thereof. Since the compound has an inhibitory effect on the Wnt/β-catenin signaling pathway and exhibits an antitumor effect, it is useful as a medicine.

9 Claims, 4 Drawing Sheets

QUINAZOLINE DERIVATIVE

TECHNICAL FIELD

The present invention relates to a medicine, in particular to a novel quinazoline derivative having an inhibitory effect on the Wnt/β-catenin signaling pathway and exhibiting an antitumor effect, or a pharmaceutically acceptable salt thereof.

BACKGROUND ART

Wnt signaling controls body axis formation and organ formation in early development; cell proliferation and cell differentiation after birth; and the like. It has been known that activation of the Wnt signaling induces various cell responses through a number of intracellular signaling pathways (Non-Patent Document 1). The most known among the Wnt signaling pathways is the β-catenin pathway. β-catenin, which is stored in the cytoplasm in a normal condition, is transferred to the nucleus by Wnt stimulation, and bound to T cell factor/lymphocyte enhancing factor (TCF/LEF) that are transcription factors to induce expression of genes such as AXIN and c-MYC. It has been known that when there is an abnormality in the Wnt signaling pathway, various diseases are caused. In particular, genetic mutations of β-catenin, APC (adenomatous polyposis coli), AXIN and the like, which are deeply related to the onset of cancer as well as are constituent proteins of the Wnt signaling pathway, have been reported in human cancer cases (Non-Patent Document 2). In these cancer cells, abnormal accumulation of β-catenin and various gene expressions promoting cell growth are observed.

It has been elucidated that the Wnt/β-catenin signaling pathway is also involved with maintenance and differentiation of undifferentiated potential of stem cells besides early development and organ formation (Non-Patent Documents 3, 4). Of the cancer cells, the presence of those cells having the similar characteristics to those of stem cells (cancer stem cells) has been reported. It is considered that cancer stem cells are sources of producing a large number of peripheral cancer cells by differentiation, while maintaining autologous cells in cancer tissue by autonomous replication. Not only in normal cells but also in cancer cells, the Wnt/β-catenin signaling pathway is involved with maintenance of their stemness. It is considered that since cancer stem cells are resistant to treatment by general anticancer drugs, a very small number of cancer stem cells survived after the anticancer drug treatment cause recurrence and metastasis of cancer (Non-Patent Documents 5, 6). Since the cancer stem cells are considered to be causes of cancerogenesis, cancer metastasis, and cancer recurrence, they are also referred to as tumor initiating cells, cancer stem-like cells, stem-like cancer cells, highly tumorigenic cells or super malignant cells.

Therefore, compounds inhibiting the Wnt/β-catenin signaling pathway are useful for treatment of diseases, with which the Wnt signaling is involved, in particular cancer, and also useful for prevention of metastasis and recurrence of tumors by targeting cancer stem cells.

Various quinazoline derivatives have hitherto been known. In addition to Patent Document 1 by the applicant, Patent Document 2, Patent Document 3 and the like have been reported. However, there is no description of quinazoline derivatives of the present invention, and there is no report stating that they inhibit the Wnt/β-catenin signaling pathway either.

PRIOR ART DOCUMENTS

Patent Documents

[Patent Document 1] WO 2009/84695 A1
[Patent Document 2] WO 2012/044090 A2
[Patent Document 3] KR 20130084474 A

Non-Patent Documents

[Non-Patent Document 1] Logan, C. Y. and Nusse, R., Annu. Rev. Cell. Dev. Biol., 2004, 20, 781-810
[Non-Patent Document 2] Clevers, H. and Nusse, R., Cell, 2012, 149, 1192-1205
[Non-Patent Document 3] Raya, T., and Clevers, H., Nature, 2005, 434, 843-850
[Non-Patent Document 4] Holland, J. D., Klaus, A., Garratt, A. N., Birchmeier, W., Curr. Opin. Cell, Biol., 2013, 25, 254-264
[Non-Patent Document 5] Dean, M., Fojo, T., Bates, S. Nat. Rev. Cancer, 2005, 5, 275-284
[Non-Patent Document 6] Li, F., Tiede, B., Massague, J., Kang, Y., Cell Res., 2007, 17, 3-14

SUMMARY OF INVENTION

Problems to be Solved by the Invention

It is an object of the present invention to provide a medicine, in particular to a novel quinazoline derivative having an inhibitory effect on the Wnt/β-catenin signaling pathway and exhibiting an antitumor effect, or a pharmaceutically acceptable salt thereof.

Means of Solving the Problems

The present invention is achieved by the following quinazoline derivatives or pharmaceutically acceptable salts thereof.
(1) A quinazoline derivative represented by the following formula (I):

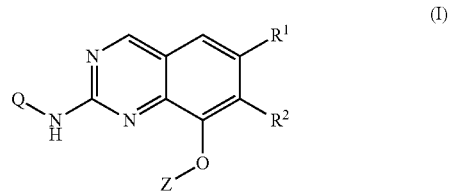

wherein $R^1$ and $R^2$ represent a hydrogen atom, a halogen atom, or a lower alkyl group optionally having a substituent; Z represents a cycloalkyl group having a substituent or a cycloalkenyl group having a substituent; and Q represents a bicyclic heteroaryl group optionally having a substituent, or a pharmaceutically acceptable salt thereof.
(2) The quinazoline derivative or pharmaceutically acceptable salt thereof of the above (1), wherein Z is a cycloalkyl group having a substituent.

(3) The quinazoline derivative or pharmaceutically acceptable salt thereof of the above (1) or (2), wherein Z is a hydroxycyclohexyl group.

(4) A quinazoline derivative represented by the following formula (Ia):

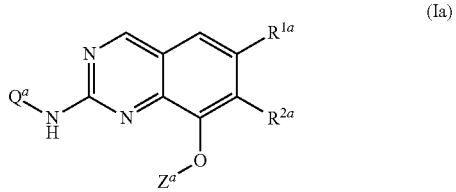

wherein $R^{1a}$ and $R^{2a}$ represent a hydrogen atom, a halogen atom, or a lower alkyl group; $Z^a$ represents a cycloalkyl group having a substituent or a cycloalkenyl group having a substituent; and $Q^a$ represents a bicyclic heteroaryl group optionally having a substituent, or a pharmaceutically acceptable salt thereof.

(5) The quinazoline derivative or pharmaceutically acceptable salt thereof of the above (4), wherein $Z^a$ is a hydroxycyclohexyl group.

Effect of the Invention

The present inventors intensively studied in order to solve the above problem, and found that novel quinazoline derivatives represented by the above (1)-(3) and pharmaceutically acceptable salts thereof have an excellent inhibitory effect on the Wnt/β-catenin signaling pathway and exhibit an antitumor effect, thereby completing the present invention. Compounds provided by the present invention are particularly useful for treatment of diseases known to be associated with abnormal cell response via the Wnt/β-catenin signaling pathway, in particular cancer, and also useful for prevention of metastasis and recurrence of tumors by targeting cancer stem cells. Furthermore, they are useful for laboratory and researching reagents as Wnt/β-catenin signaling pathway inhibitors.

DESCRIPTION OF EMBODIMENTS

Figure 1:
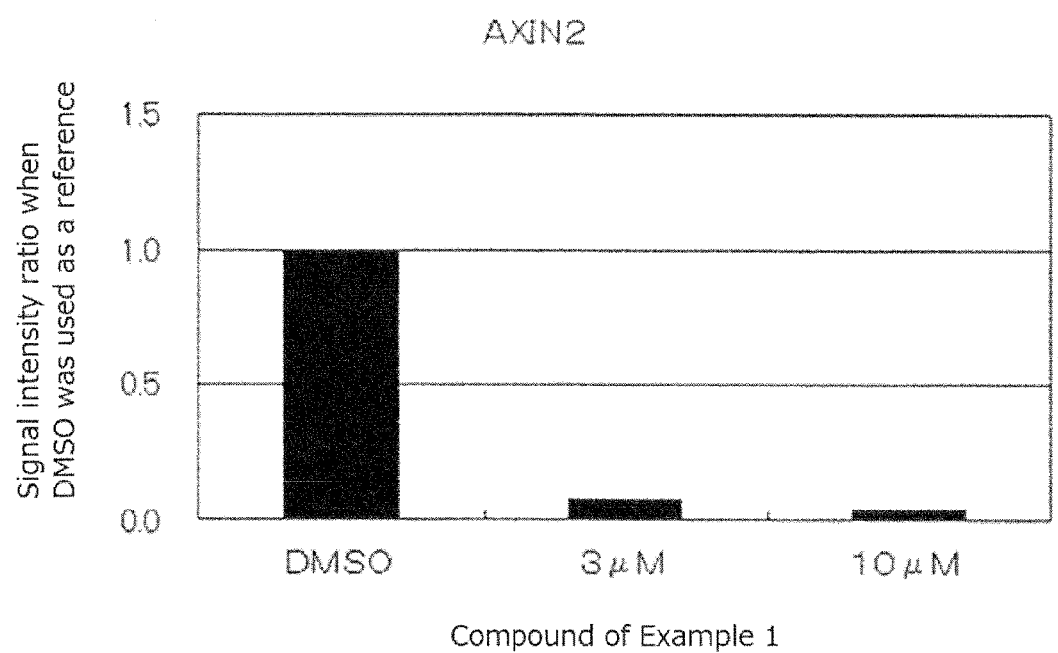
FIG. 1 shows that the compound of Example 1 inhibits AXIN 2 gene expression in HCT116 colorectal cancer cells in a concentration-dependent manner (Text Example 2).

The present invention will hereinafter be described in detail.

A novel quinazoline derivative of the present invention is a compound represented by the following formula (I):

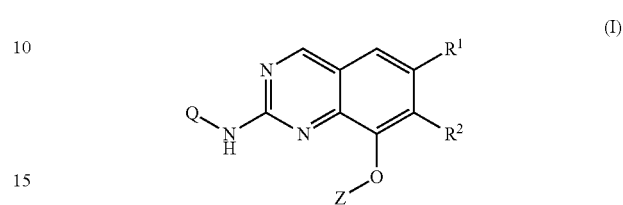

wherein $R^1$ and $R^2$ represent a hydrogen atom, a halogen atom, or a lower alkyl group optionally having a substituent; Z represents a cycloalkyl group having a substituent or a cycloalkenyl group having a substituent; and Q represents a bicyclic heteroaryl group optionally having a substituent, or a pharmaceutically acceptable salt thereof.

In the above formula (I), examples of the halogen atom include fluorine, chlorine, bromine and the like.

The lower alkyl moiety in the lower alkyl group optionally having a substituent may be any linear or branched alkyl group having 1 to 4 carbon atoms. Examples thereof include a methyl group, isopropyl group, tert-butyl group, and the like.

The cycloalkyl moiety in the cycloalkyl group having a substituent may be any cyclic alkyl group having 3 to 7 carbon atoms. Examples thereof include a cyclopropyl group, cyclobutyl group, cyclopentyl group, cyclohexyl group, and the like.

The cycloalkenyl moiety in the cycloalkenyl group having a substituent may be any cyclic alkenyl group having 5 to 7 carbon atoms. Examples thereof include a cyclopentenyl group, cyclohexenyl group, and the like.

The bicyclic heteroaryl moiety in the bicyclic heteroaryl group optionally having a substituent may be, for example, any 4- to 6-membered condensed bicyclic aromatic hetero-ring group containing at least one hetero atom selected from the group consisting of a nitrogen atom, a sulfur atom and an oxygen atom. Examples thereof include a tetrahydroisoquinolyl group, benzothiophenyl group, benzimidazolyl group, benzoxazolyl group, benzothiazolyl group, indolyl group, benzotriazolyl group, quinolyl group, isoquinolyl group, quinazolyl group, indazolyl group, and the like.

Unless otherwise stated, the substituents of the lower alkyl group optionally having a substituent, the cycloalkyl group having a substituent, the cycloalkenyl group having a substituent, and the bicyclic heteroaryl group optionally having a substituent may have one or two or more of any of the substituents at any chemically possible positions. When the substituents are two or more in number, the respective substituents may be the same or different. Examples thereof include a halogen atom, substituted or non-substituted alkyl group, cycloalkyl group, substituted or non-substituted alkoxy group, substituted or non-substituted amino group, nitro group, cyano group, hydroxy group, substituted or non-substituted alkylamino group, substituted or non-substituted carbamoyl group, carboxyl group, morpholinyl group, formyl group, acetyl group, mesyl group, benzoyl group, substituted or non-substituted acylamino group, and the like.

More specifically, examples of the substituent of "the lower alkyl group optionally having a substituent" include a halogen atom, $C_1$-$C_4$ alkoxy group, amino group, $C_1$-$C_4$ alkylamino group, hydroxy group, carbamoyl group, carboxyl group, formyl group, acetyl group, mesyl group, benzoyl group, acylamino group, and the like.

Examples of the substituent of "the cycloalkyl group having a substituent" or "the cycloalkenyl group having a substituent" include a halogen atom, $C_1$-$C_4$ alkyl group, $C_1$-$C_4$ alkoxy group, amino group, $C_1$-$C_4$ alkylamino group optionally substituted with a sulfonyl group, hydroxy group, carbamoyl group, carboxyl group, formyl group, acetyl group, mesyl group, benzoyl group, acylamino group, and the like. In particular, hydroxy group and amino group are preferred.

Examples of the substituent of "the bicyclic heteroaryl group optionally having a substituent" include a halogen atom, a $C_1$-$C_4$ alkyl group optionally substituted with (a hydroxy group, a methoxy group or a pyrrolidinyl group), a $C_3$-$C_5$ cycloalkyl group, a $C_1$-$C_4$ alkoxy group, an amino group, a $C_1$-$C_4$ alkylamino group, a di($C_1$-$C_4$ alkyl)amino group, a hydroxy group, a carbamoyl group, a carboxyl group, a morpholinyl group, a pyrrolidinyl group, a formyl group, an acetyl group, a mesyl group, a benzoyl group, an acylamino group, and the like.

The present invention also provides a novel quinazoline derivative (Ia):

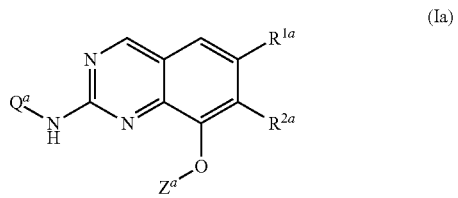

(Ia)

wherein $R^{1a}$ and $R^{2a}$ represent a hydrogen atom, a halogen atom, or a lower alkyl group; $Z^a$ represents a cycloalkyl group having a substituent or a cycloalkenyl group having a substituent; and $Q^a$ represents a bicyclic heteroaryl group optionally having a substituent, or a pharmaceutically acceptable salt thereof.

In the above formula (Ia), the halogen atom, the lower alkyl group, the cycloalkyl group, and the cycloalkenyl group are the same as those of the above formula (I).

The bicyclic heteroaryl group of $Q^a$ may be any 4- to 6-membered condensed bicyclic aromatic hetero-ring group optionally containing at least one hetero atom selected from, in addition to a nitrogen atom, a sulfur atom and an oxygen atom. Examples thereof include a benzimidazolyl group, a benzoxazolyl group, a benzothiazolyl group, a quinolyl group, an isoquinolyl group, a quinazolyl group, an indazolyl group, and the like.

Examples of the substituent of "the bicyclic heteroaryl group optionally having a substituent" in $Q^a$ include a halogen atom, a $C_1$-$C_4$ alkyl group optionally substituted with (a halogen atom, a hydroxy group, a methoxy group, a dimethylamino group or a pyrrolidinyl group), a $C_3$-$C_5$ cycloalkyl group, a $C_1$-$C_4$ alkoxy group, an amino group, a $C_1$-$C_4$ alkylamino group, a hydroxy group, a morpholinyl group, and the like.

$Q^a$ is preferably an indazolyl group or a benzimidazolyl group optionally substituted with a lower alkyl group, and further the lower alkyl group may be substituted with a hydroxy group.

The substituent of "the cycloalkyl group having a substituent" and "the cycloalkenyl group having a substituent" is selected from hydroxy and amino groups.

The following description regarding the compound (I) of the present invention is also applied to the compound (Ia) of the present invention.

The compound (I) according to the present invention may in some cases exist in isomers depending on the type of substituent, for example. In the present specification, the compound according to the present invention may be described in only one form of isomers, but the present invention includes all the isomers (geometric isomers, optical isomers, tautomers and the like) that can be structurally derived, and also includes single isomers, or mixtures of them.

Examples of the pharmaceutically acceptable salt of the compound (I) of the present invention include inorganic salts derived from hydrochloric acid, sulfuric acid, carbonic acid, phosphoric acid or the like; and organic acid salts derived from fumaric acid, maleic acid, methanesulfonic acid, p-toluenesulfonic acid or the like. Further, alkali metal salts derived from sodium, potassium or the like; alkaline earth metal salts derived from magnesium, calcium or the like; organic amine salts derived from a lower alkylamine, a lower alcohol amine or the like; basic amino acid salts derived from lysine, arginine, ornithine or the like, and, in addition to the above, ammonium salts and the like are also included in the present invention.

In the compound of the present invention and pharmaceutically acceptable salt thereof, both of an intramolecular salt thereof and a solvate thereof such as a hydrate thereof are included.

The compounds (I) of the present invention and pharmaceutically acceptable salts thereof can be produced, for example, by the following methods. In the production methods shown below, when a defined group is changed under conditions of a method of implementation, or the group is unsuitable for carrying out the method, the intended compounds or pharmaceutically acceptable salts thereof can be easily obtained by a method conventionally used in synthetic organic chemistry, for example, by using means such as protection and de-protection of functional groups [T. W. Greene, Protective Groups in Organic Synthesis, $3^{rd}$ Edition, John Wiley & Sons, Inc., 1999], and the like. Also an order of steps introducing a substituent may be changed, if necessary.

The meanings of abbreviations and symbols used in the following description are as follows:
DCM: dichloromethane
THF: tetrahydrofuran
DMF: dimethylformamide
DMSO: dimethylsulfoxide
$CDCl_3$: heavy chloroform
Production Method of the Compound (I) of the Present Invention The compound of the present invention represented by the formula (I) can be produced, for example, by Scheme 1.

[Scheme 1]

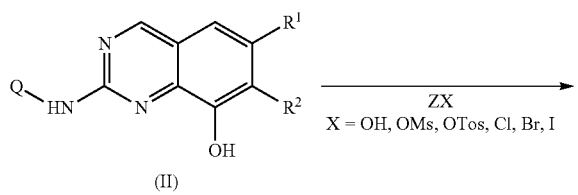

(II)

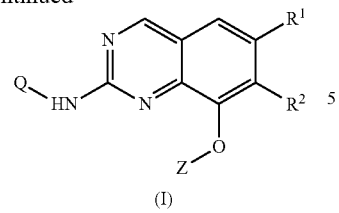

(I)

wherein R[1], R[2], Q and Z are the same as defined above.

A compound (I) can be produced by nucleophilic substitution reaction of a hydroxyl group of a compound (II) with a Z group-introducing agent (ZX).

When X is an appropriate leaving group, for example, a mesylated or tosylated hydroxyl group, a chloro atom, a bromo atom, an iodo atom or the like, the compound (I) can be obtained by reacting the compound (II) under heating with 1 to 5 molar equivalents, preferably 1 to 1.5 molar equivalents of the Z group-introducing agent in a solvent in the presence of 1 to 5 molar equivalents, preferably 1 to 3.5 molar equivalents of a base such as cesium carbonate. The solvent is not particularly limited as long as it is inactive to the reaction. DMSO or DMF can be preferably used. The reaction can be carried out by heating the mixture at 80-180° C. for 1-24 hours, preferably at 100-150° C. for 1-4 hours.

The compound (I) can also be produced by reacting a hydroxyl group of the compound (II) with the Z group-introducing agent having a hydroxyl group using Mitsunobu reaction. That is, the compound (I) can be obtained by reacting the compound (II) under heating with 1 to 5 molar equivalents, preferably 1 to 2 molar equivalents of the Z group-introducing agent having an alcohol group in a solvent in the presence of 1 to 10 molar equivalents, preferably 1 to 5 molar equivalents of a Mitsunobu reagent, for example, cyanomethylenetributylphosphoran.

The solvent is not particularly limited as long as it is inactive to the reaction. Preferably, 1,4-dioxane or THF can be used. The reaction can be carried out by heating the mixture at 50-150° C. for 1-24 hours, for example, at 100° C. for 3-16 hours.

The Z group-introducing agent can be obtained as a commercially available product, or by a publicly known method or a method based thereon.

When the above coupling reaction is carried out, the compound (I) can also be obtained by protection and de-protection of functional groups existing in Q and the Z group-introducing agent by combined use of methods conventionally used in synthetic organic chemistry, as necessary. For example, protection and de-protection of the functional groups such as hydroxyl group and amino group [T. W. Greene, Protective Groups in Organic Synthesis, 3rd Edition, John Wiley & Sons Inc., 1999] can be used.

The compound (II) used as a raw material of Scheme 1 can be produced by a method shown in, for example, Scheme 2.

[Scheme 2]

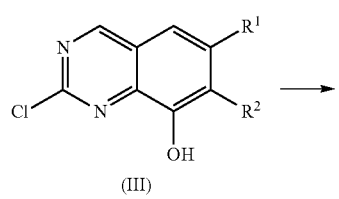

(III)

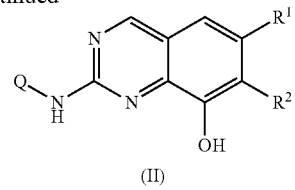

(II)

wherein R[1], R[2] and Q are the same as defined above.

The compound (II) can be obtained by reacting a compound (III) under heating with 1 to 5 molar equivalents, preferably 1 to 1.5 molar equivalents of an amine (Q-NH$_2$) in a solvent, in the presence of an acid catalyst such as hydrochloric acid as necessary. The solvent is not particularly limited as long as it is inactive to the reaction. For example, a lower alcohol, preferably ethanol, 2-propanol or 1-butanol can be used. The reaction can be carried out by heating the mixture at 80-150° C. for 3-24 hours, for example, at 100-110° C. for 6-16 hours.

The amine (Q-NH$_2$), one of the raw materials of Scheme 1, can be obtained as a commercially available product (for example, a product of Sigma-Aldrich Co. LLC.), or by a publicly known method or a method based thereon.

Among the compounds (III) used as a raw material of Scheme 2, a compound (III-a) in which R[1] and R[2] are each a hydrogen atom, and a compound (III-b) in which R[1] is a hydrogen atom, and R[2] is a bromine atom can be produced, for example, by a method shown in Scheme 3.

[Scheme 3]

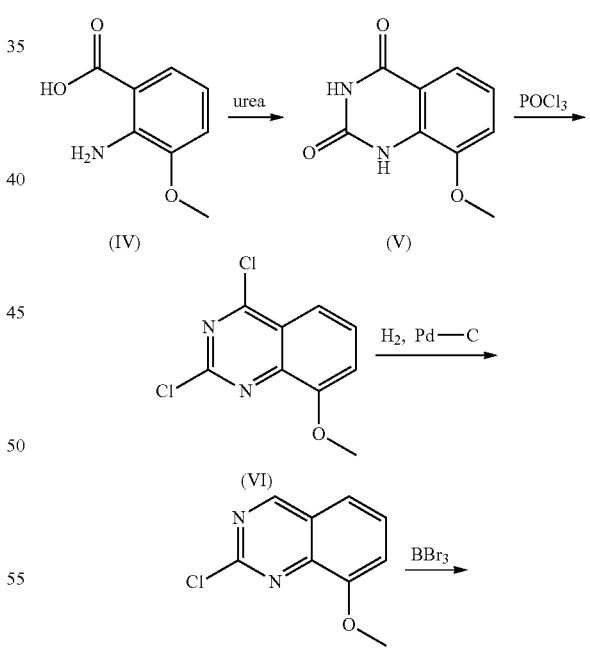

The compound (III-a) can be produced from 2-amino-3-methoxy benzoic acid (IV) as a starting raw material. That is, a compound (V) obtained by reacting 2-amino-3-methoxy benzoic acid (IV) with urea under heating is treated with phosphoryl chloride in the presence of N,N-dimethylaniline so as to give a compound (VI). The resultant compound (VI) is reacted with palladium-carbon under a hydrogen atmosphere and under basic conditions to selectively remove a chloro atom at position 4. The resultant compound (VII) is treated with boron tribromide to obtain a compound (III-a).

The compound (III-b) can be obtained by reacting the compound (III-a) with N-bromosuccinimide (NBS) in a solvent in the presence of diisopropylamine.

Among the compounds (III) used as a raw material of Scheme 2, a compound (III-c) in which $R^1$ is a bromine atom, and $R^2$ is a hydrogen atom can be produced, for example, by a method shown in Scheme 4.

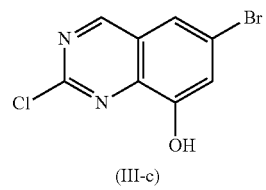

(III-c)

The compound (III-c) can be obtained in the following manner: 2-amino-3-methoxy benzoic acid (1V) is brominated with bromine. A carboxylic acid of a compound (VIII) thus obtained is reduced with borane, and converted into an alcohol. Then, a compound (X) obtained by oxidizing the alcohol again into an aldehyde is reacted with urea under heating to obtain a compound (XI). Then, the compound (XI) is treated with phosphoryl chloride, and converted into a compound (XII). Thereafter, the compound (XII) is treated with boron tribromide.

Among the compounds (III) used as a raw material of Scheme 2, a compound (III-d) in which $R^1$ is a fluorine atom, and $R^2$ is a hydrogen atom can be produced, for example, by a method shown in Scheme 5.

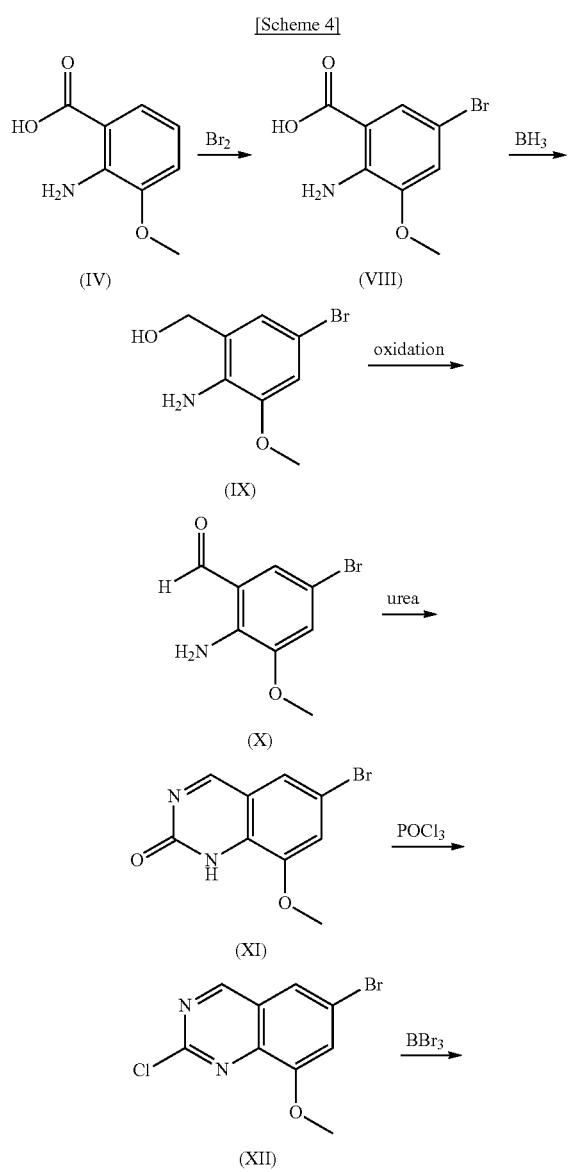

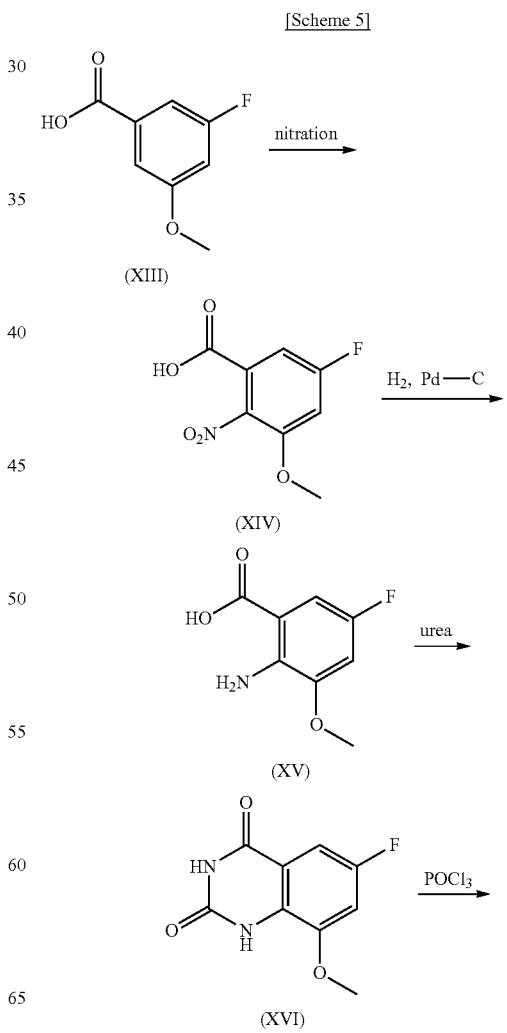

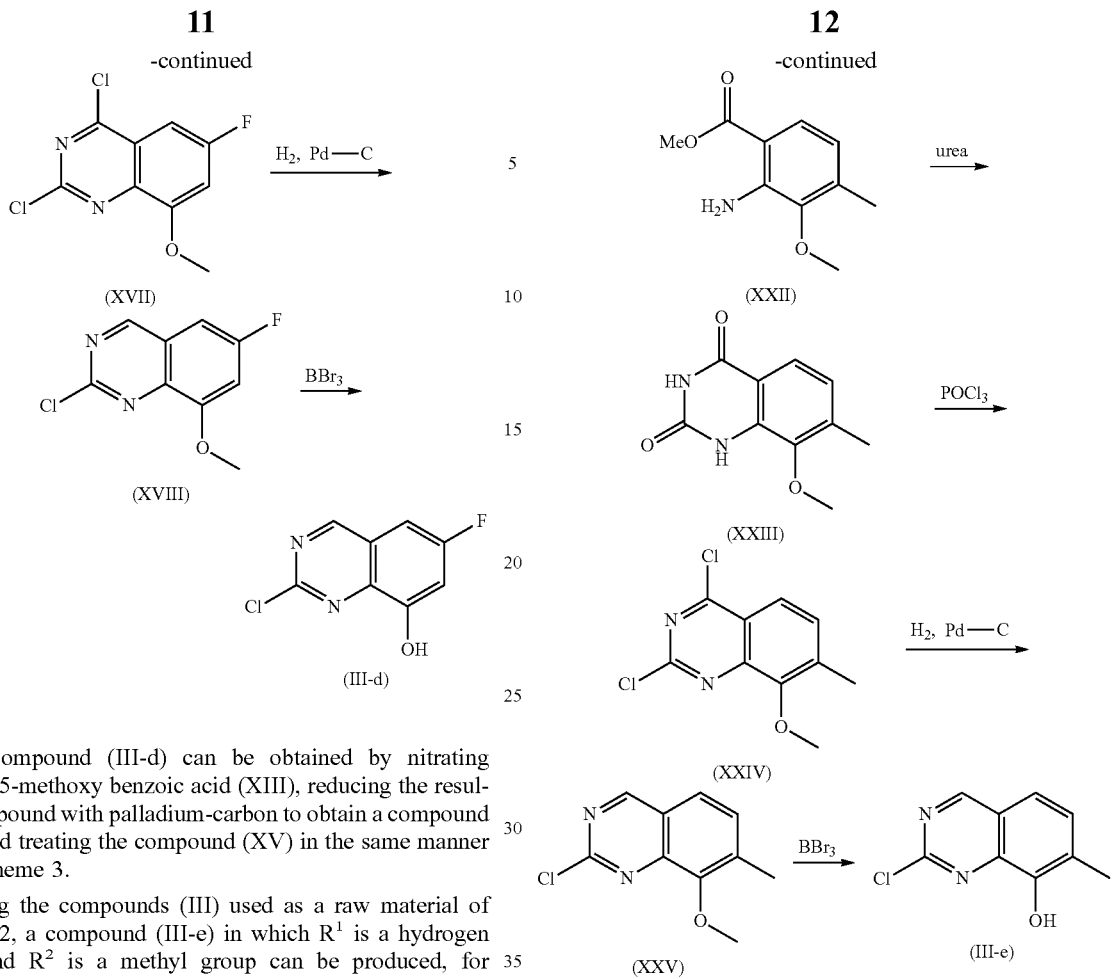

The compound (III-d) can be obtained by nitrating 3-fluoro-5-methoxy benzoic acid (XIII), reducing the resultant compound with palladium-carbon to obtain a compound (XV), and treating the compound (XV) in the same manner as in Scheme 3.

Among the compounds (III) used as a raw material of Scheme 2, a compound (III-e) in which $R^1$ is a hydrogen atom, and $R^2$ is a methyl group can be produced, for example, by a method shown in Scheme 6.

[Scheme 6]

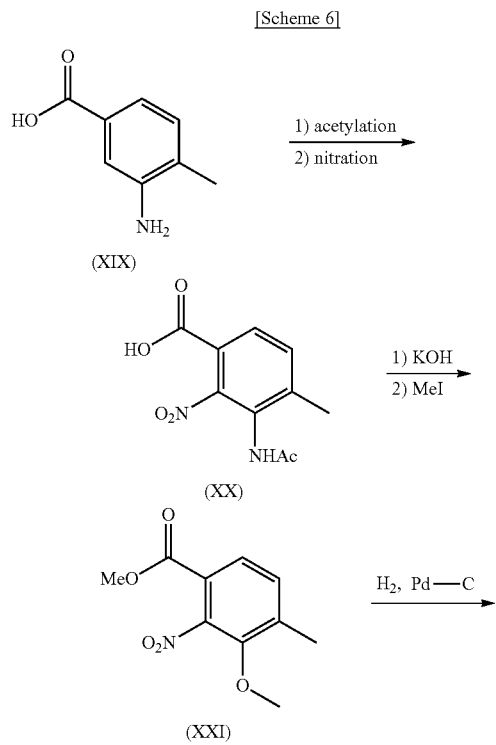

The compound (III-e) can be produced in the following manner: A compound (XX) obtained by acetylation and nitration of 3-amino-4-methyl benzoic acid (XIX) is treated with potassium hydroxide to obtain a phenol compound. The resultant phenol compound is methylated and further reduced with palladium-carbon to synthesize a compound (XXII). The compound (XXII) is treated in the same manner as in Scheme 3.

The compound (I) of the present invention can be obtained by combined use of the above methods as necessary, and carrying out the methods usually used in synthetic organic chemistry (for example, an alkylation reaction of an amino group; a reaction of oxidizing an alkylthio group to form a sulfoxide group or a sulfone group; a reaction of converting an alkoxy group into a hydroxyl group or vice versa).

[Uses of the Compounds (I) of the Present Invention]

The compounds (I) of the present invention or pharmaceutically acceptable salts thereof can be prepared into the form of a conventional pharmaceutical preparation (pharmaceutical composition) suitable for oral administration, parenteral administration or local administration.

The preparation for oral administration includes solid preparations such as a tablet, a granule, powder, a capsule; and liquid preparations such as syrup. These preparations can be prepared by a conventional method. The solid preparations can be prepared by using conventional pharmaceutical carriers such as lactose, starch such as corn starch, crystalline cellulose such as microcrystalline cellulose, hydroxypropyl cellulose, calcium carboxymethyl cellulose, talc and magnesium stearate. The capsule can be prepared by encapsulating the thus prepared granules or powder. The syrup can be prepared by dissolving or suspending the compound (I) of the present invention or pharmaceutically acceptable salt thereof in an aqueous solution containing sucrose, carboxymethyl cellulose and the like.

The preparation for parenteral administration includes an injection material such as intravenous feeding. An injectable preparation can also be prepared by a conventional method. A tonicity agent (for example, mannitol, sodium chloride, glucose, sorbitol, glycerol, xylitol, fructose, maltose, mannose), a stabilizer (for example, sodium sulfite, albumin), and an antiseptic agent (for example, benzyl alcohol, methyl p-oxybenzoate) are incorporated into the injectable preparation.

Doses of the compound (I) of the present invention or pharmaceutically acceptable salt can be changed depending on the severity of disease, the age and body weight of a patient, the dosage form, and the like. Usually, a daily dose is in a range of 1 mg-1,000 mg in adults, which can be administered once or dividedly administered twice or three times, by oral or parenteral administration.

The compounds (I) of the present invention or pharmaceutically acceptable salts thereof can also be used for laboratory and researching reagents as Wnt/β-catenin signaling pathway inhibitors.

Furthermore, compounds which are radiolabeled with the compound (I) of the present invention can also be used as molecular probes for PET.

EXAMPLES

The present invention will further be specifically described below by citing Examples, Test Examples and the like. However, it should not be construed that the present invention is limited by these Examples.

Identification of compounds is performed by hydrogen nuclear magnetic resonance ($^1$H-NMR) spectroscopy and mass spectroscopy (MS). Unless otherwise particularly specified, $^1$H-NMR was measured at 400 MHz. Exchangeable hydrogen is sometimes not clearly observed depending on the compounds or the measuring conditions. The term "br" means a broad signal.

Preparative HPLC chromatography was performed in a gradient mode, using a commercially available ODS column and water/methanol (containing formic acid) as an eluent.

Reference Example 1

Production of 2-chloroquinazolin-8-ol

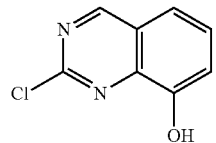 [SMILES: Oc1cccc2cnc(Cl)nc12]

To a DCM solution (91 mL) of 2-chloro-8-methoxyquinazoline (8.85 g, 45.0 mmol), boron tribromide (1M/DCM, 100 mL) was added dropwise under ice cooling, and then the mixture was stirred at room temperature for 16 hours. The reaction mixture was cooled to −5° C., and a precipitated solid was filtered. The precipitated solid was washed with saturated sodium hydrogen carbonate to give 5.84 g of a crude product of 2-chloroquinazolin-8-ol.

$^1$H-NMR (DMSO-do) δ(ppm): 10.58 (s, 1H), 9.53 (s, 1H), 7.6-7.65 (m, 2H), 7.36-7.42 (m, 1H);
LC-MS (m/z) 181.0 [M+H]$^+$.

Reference Example 2

Production of trans-4-tert-butyldimethylsilyloxycyclohexyl methanesulfonate

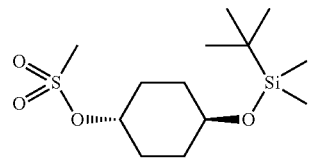 [SMILES: CC(C)(C)[Si](C)(C)O[C@H]1CC[C@H](OS(C)(=O)=O)CC1]

(First Step)
To a DMF solution (45 mL) of trans-cyclohexane-1,4-diol (5.00 g, 43.0 mmol) and 4-dimethylaminopyridine (0.27 g, 2.21 mmol), triethylamine (6 mL, 43.0 mmol) and tert-butyldimethylsilyl chloride (6.49 g, 43.0 mmol) were added under ice cooling, and the mixture was stirred at room temperature for 25 minutes. After the reaction solution was diluted with ethyl acetate, an organic layer obtained by washing the resultant solution with water twice was dried over sodium sulfate. The residue obtained by distilling off the solvent under reduced pressure was purified with column chromatography (silica gel, hexane/ethyl acetate) to give trans-4-tert-butyldimethylsilyloxycyclohexanol (5.32 g).

$^1$H-NMR (DMSO-d6) δ(ppm): 4.45 (d, J=4.2 Hz, 1H), 3.54-3.66 (m, 1H), 3.36-3.46 (m, 1H), 1.7-1.8 (m, 4H), 1.12-1.3 (m, 4H), 0.84 (s, 9H), 0.02 (s, 6H).

(Second Step)
To a DCM solution (77 mL) of trans-4-tert-butyldimethylsilyloxycyclohexanol (5.32 g, 23.1 mmol) and triethylamine (3.85 mL, 27.7 mmol), methanesulfonyl chloride (1.97 mL, 25.4 mmol) was added dropwise under ice cooling, and the mixture was stirred at room temperature for 16 hours. After saturated sodium hydrogen carbonate was added thereto to stop the reaction, the reaction mixture was extracted twice with chloroform. The obtained organic layers were combined, sequentially washed with a saturated aqueous solution of sodium hydrogen carbonate, water, and dried over sodium sulfate. Thereafter, the solvent was distilled off under reduced pressure. The residue was purified with column chromatography (silica gel, hexane/ethyl acetate) to give the title compound (6.71 g).

$^1$H-(DMSO-d$_6$) δ(ppm): 4.6-4.7 (m, 1H), 3.7-3.8 (m, 1H), 3.16 (s, 3H), 1.92-2.0 (m, 2H), 1.7-1.8 (m, 2H), 1.5-1.65 (m, 2H), 1.32-1.45 (m, 2H), 0.86 (s, 9H), 0.04 (s, 6H).

Example 1

Production of cis-4-({2-[(1H-benzo[d]imidazol-6-yl)amino]quinazolyn-8-yl}oxy)cyclohexanol

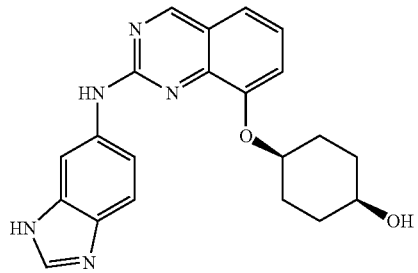 [SMILES: O[C@H]1CC[C@@H](Oc2cccc3cnc(Nc4ccc5nc[nH]c5c4)nc23)CC1]

(First Step)

A 2-propanol solution (15 mL) of the compound of Reference Example 1 (0.97 g, 5.26 mmol) and 1H-benzimidazole-6-amine (0.70 g, 5.26 mmol) was stirred at 100-110° C. for 16 hours. After the solution was cooled to room temperature, a precipitated solid was filtered. After washed with 2-propanol, the precipitated solid was dried to give 2-[(1H-benzo[d]imidazol-6-yl)amino]quinazolin-8-ol (1.07 g).

$^1$H-NMR (DMSO-$d_6$) δ(ppm): 10.31 (s, 1H), 9.6-9.75 (br, 1H), 9.50 (s, 1H), 9.31 (s, 1H), 8.98 (d, J=1.1 Hz, 1H), 7.96 (dd, J=9.0, 1.7 Hz, 1H), 7.76 (d, J=7.9 Hz, 1H), 7.42 (dd, J=7.5, 1.1 Hz, 1H), 7.2-7.35 (m, 2H);

LC-MS (m/z) 278.2 [M+H].

(Second Step)

To a DMSO suspension (40 mL) of 2-[(1H-benzo[d]imidazol-6-yl)amino]quinazolin-8-ol (1.50 g, 5.41 mmol) and the compound of Reference Example 2 (2.50 g, 8.12 mmol), cesium carbonate (5.45 g, 16.78 mmol) was added. Thereafter, the mixture was stirred at 130° C. for one hour. The reaction mixture was diluted with ethyl acetate (50 mL) and THF (50 mL), and ice water (25 mL) was then added thereto. After an organic layer was separated, and the obtained organic layer was dried over sodium sulfate, the solvent was distilled off under reduced pressure. The residue was purified with column chromatography (silica gel, hexane/ethyl acetate) to give N-(1H-benzo[d]imidazol-6-yl)-8-({cis-4-[(tert-butyldimethylsilyl)oxy)cyclohexyl]oxy}quinazoline-2-amine (1.16 g).

$^1$H-NMR (DMSO-$d_6$) δ(ppm): 11.99-12.32 (m, 1H), 9.72-9.90 (m, 1H), 9.16-9.31 (m, 1H), 8.28-8.37 (m, 1H), 7.99-8.18 (m, 2H), 7.38-7.63 (m, 2H), 7.30-7.38 (m, 1H), 7.16-7.30 (m, 1H), 4.76 (br, 1H), 3.84 (br, 1H), 1.92-2.07 (m, 2H), 1.67-1.91 (m, 4H), 1.56-1.67 (m, 2H), 0.87 (s, 9H), 0.06 (s, 6H);

LC-MS (m/z) 490.2 [M+H]$^+$.

(Third Step)

To a 1,4-dioxane solution (20 mL) of N-(1H-benzo[d]imidazol-6-yl)-8-({cis-4-[(tert-butyldimethylsilyl)oxy)cyclohexyl]oxy}quinazoline-2-amine (4.0 g, 8.18 mmol), 4N—HCL/1,4-dioxane (20 mL) was added at 0° C., and then the mixture was stirred at room temperature for one hour. To the residue obtained by distilling off the solvent under reduced pressure, a saturated aqueous solution of sodium hydrogen carbonate (25 mL) was added. A precipitated solid was filtered. After washed with ethyl acetate (20 mL), the precipitated solid was dried to give the title compound (2.0 g).

$^1$H-NMR (DMSO-$d_6$) δ(ppm): 12.29-12.54 (m, 1H), 9.73-10.0 (m, 1H), 9.15-9.3 (m, 1H), 8.65-9.11 (m, 1H), 7.98-8.27 (m, 1H), 7.52-7.69 (m, 2H), 7.4-7.52 (m, 1H), 7.36 (dd, J=7.9, 1.2 Hz, 1H), 7.26 (t, J=7.9 Hz, 1H), 5.51-5.9 (m, 1H), 4.88 (s, 1H), 3.45-3.85 (m, 1H), 1.82-2.13 (m, 4H), 1.49-1.85 (m, 4H);

LC-MS (m/z) 376.2 [M+H]$^+$.

Examples 2-46

Compounds in the following Examples [Table 1] were produced using the respective corresponding raw materials (commercially available products, or compounds derived from commercially available compounds by a publicly known method or a method based thereon) according to the methods described in the above Example, and, optionally in combination with methods usually used in synthetic organic chemistry, as necessary.

Also, physicochemical data of the respective compounds are shown in [Table 2].

TABLE 1

| Ex. | Structure | Name |
|---|---|---|
| 2 | 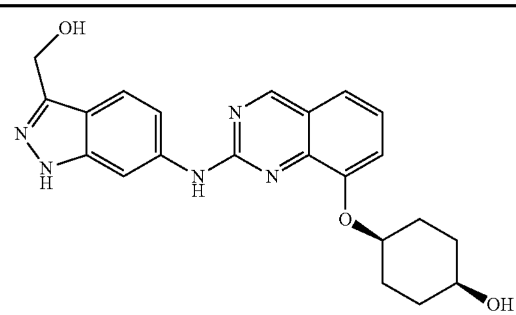 | cis-4-[(2-{[3-(hydroxymethyl)-1H-indazol-6-yl]amino}quinazolin-8-yl)oxy]cyclohexanol |
| 3 | 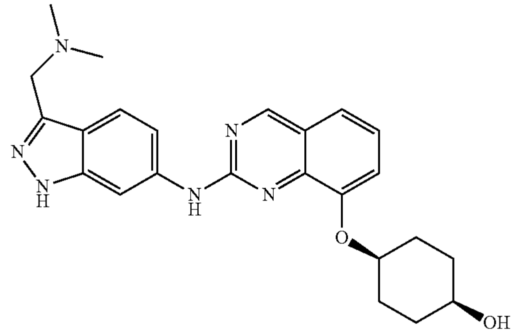 [SMILES: CN(C)Cc1n[nH]c2cc(Nc3ncc4cccc(O[C@H]5CC[C@@H](O)CC5)c4n3)ccc12] | cis-4-{[2-({3-[(dimethylamino)methyl]-1H-indazol-6-yl}amino)quinazolin-8-yl]oxy}cyclohexanol |

TABLE 1-continued

| Ex. | Structure | Name |
|---|---|---|
| 4 | 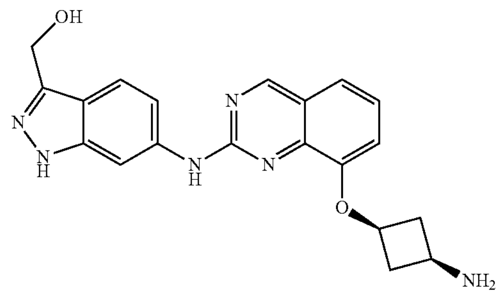 [SMILES: N[C@H]1C[C@@H](Oc2cccc3cnc(Nc4ccc5c(CO)n[nH]c5c4)nc23)C1] | (6-{[8-(cis-3-aminocyclobutoxy)quinazolin-2-yl]amino}-1H-indazol-3-yl)methanol |
| 5 | 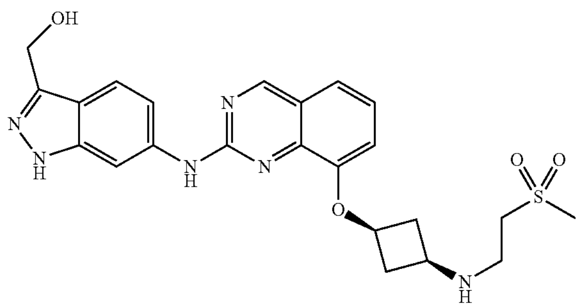 [SMILES: CS(=O)(=O)CCN[C@H]1C[C@@H](Oc2cccc3cnc(Nc4ccc5c(CO)n[nH]c5c4)nc23)C1] | {6-([8-(cis-3-{[2-(methylsulfonyl)ethyl]amino]cyclobutoxy}quinazolin-2-yl)amino]-1H-indazol-3-yl}methanol |
| 6 | 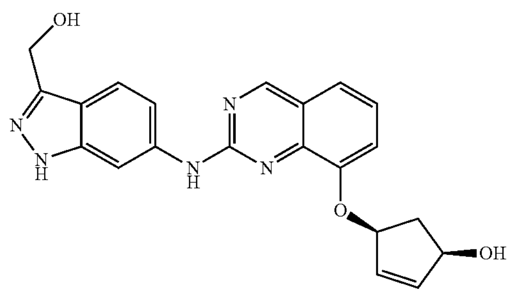 [SMILES: OCc1n[nH]c2cc(Nc3ncc4cccc(O[C@@H]5C=C[C@H](O)C5)c4n3)ccc12] | cis-4-[(2-{[3-(hydroxymethyl)-1H-indazol-6-yl]amino}quinazolin-8-yl)oxy]cyclopent-2-enol |
| 7 | 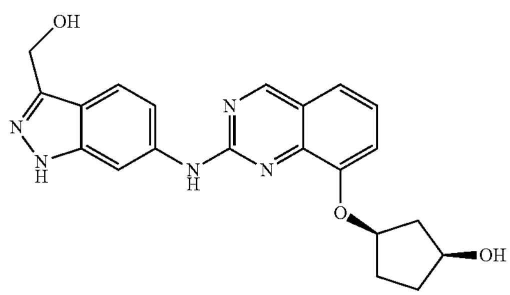 [SMILES: OCc1n[nH]c2cc(Nc3ncc4cccc(O[C@@H]5CC[C@H](O)C5)c4n3)ccc12] | cis-3-[(2-{[3-(hydroxymethyl)-1H-indazol-6-yl]amino}quinazolin-8-yl)oxy]cyclopentanol |
| 8 | 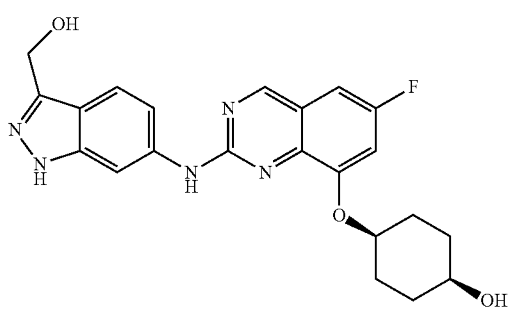 [SMILES: OCc1n[nH]c2cc(Nc3ncc4cc(F)cc(O[C@H]5CC[C@@H](O)CC5)c4n3)ccc12] | cis-4-[(6-fluoro-2-{[3-(hydroxymethyl)-1H-indazol-6-yl]amino}quinazolin-8-yl)oxy]cyclohexanol |

TABLE 1-continued

| Ex. | Structure | Name |
|---|---|---|
| 9 | 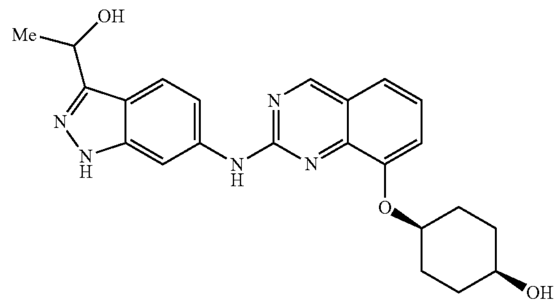 [SMILES: CC(O)c1n[nH]c2cc(Nc3ncc4cccc(O[C@H]5CC[C@@H](O)CC5)c4n3)ccc12] | cis-4-[(2-{[3-(1-hydroxyethyl)-1H-indazol-6-yl]amino}quinazolin-8-yl)oxy]cyclohexanol |
| 10 | 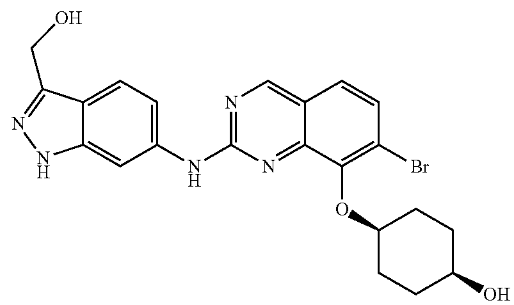 [SMILES: OCc1n[nH]c2cc(Nc3ncc4ccc(Br)c(O[C@H]5CC[C@@H](O)CC5)c4n3)ccc12] | cis-4-[(7-bromo-2-{[3-(hydroxymethyl)-1H-indazol-6-yl]amino}quinazolin-8-yl)oxy]cyclohexanol |
| 11 | 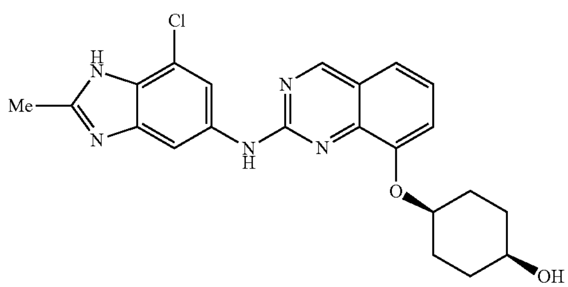 [SMILES: Cc1nc2cc(Nc3ncc4cccc(O[C@H]5CC[C@@H](O)CC5)c4n3)cc(Cl)c2[nH]1] | cis-4-({2-[(7-chloro-2-methyl-1H-benzo[d]imidazol-5-yl)amino]quinazolin-8-yl}oxy)cyclohexanol |
| 12 | 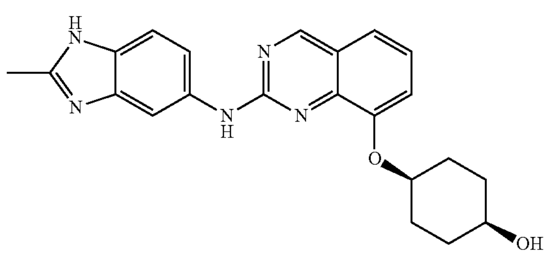 [SMILES: Cc1nc2cc(Nc3ncc4cccc(O[C@H]5CC[C@@H](O)CC5)c4n3)ccc2[nH]1] | cis-4-({2-[(2-methyl-1H-benzo[d]imidazol-5-yl)amino]quinazolin-8-yl}oxy)cyclohexanol |
| 13 | 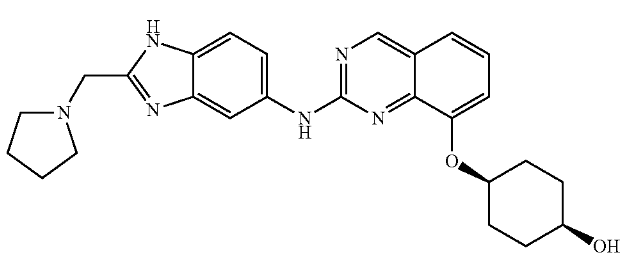 [SMILES: O[C@H]1CC[C@@H](Oc2cccc3cnc(Nc4ccc5[nH]c(CN6CCCC6)nc5c4)nc23)CC1] | cis-4-[(2-{[2-(pyrrolidin-1-ylmethyl)-1H-benzo[d]imidazol-5-yl]amino}quinazolin-8-yl)oxy]cyclohexanol |

TABLE 1-continued

| Ex. | Structure | Name |
|---|---|---|
| 14 | 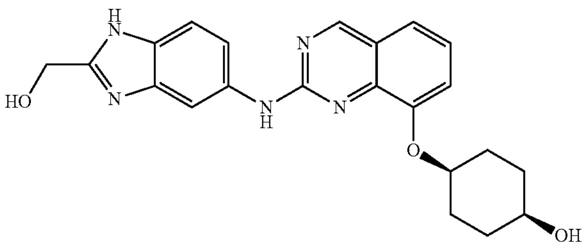 [SMILES: OCc1nc2cc(Nc3ncc4cccc(O[C@H]5CC[C@@H](O)CC5)c4n3)ccc2[nH]1] | cis-4-[(2-{[2-(hydroxymethyl)-1H-benzo[d]imidazol-5-yl]amino}quinazolin-8-yl)oxy]cyclohexanol |
| 15 | 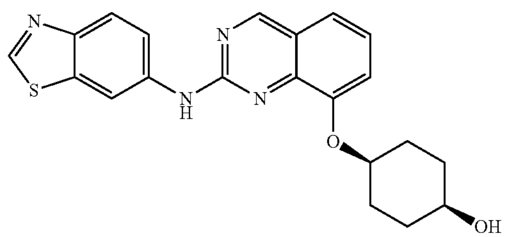 [SMILES: O[C@H]1CC[C@@H](Oc2cccc3cnc(Nc4ccc5ncsc5c4)nc23)CC1] | cis-4-{[2-(benzo[d]thiazol-6-ylamino)quinazolin-8-yl]oxy}cyclohexanol |
| 16 | 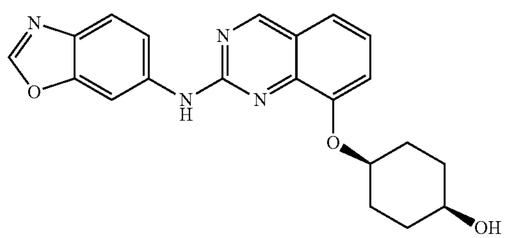 | cis-4-{[2-(benzo[d]oxazol-6-ylamino)quinazolin-8-yl]oxy}cyclohexanol |
| 17 | 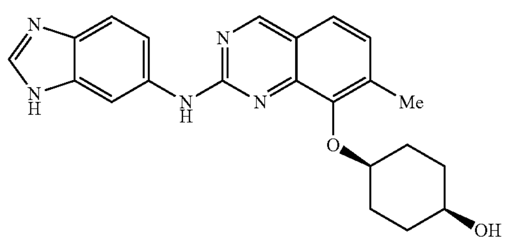 [SMILES: Cc1ccc2cnc(Nc3ccc4nc[nH]c4c3)nc2c1O[C@H]1CC[C@@H](O)CC1] | cis-4-({2-[(1H-benzo[d]imidazol-6-yl)amino]-7-methylquinazolin-8-yl}oxy)cyclohexanol |
| 18 | 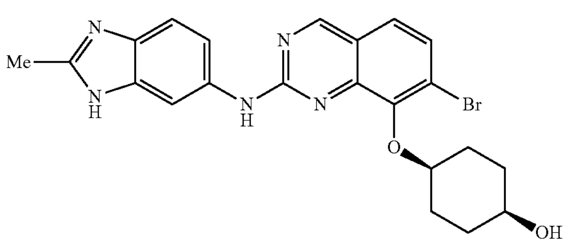 [SMILES: Cc1nc2ccc(Nc3ncc4ccc(Br)c(O[C@H]5CC[C@@H](O)CC5)c4n3)cc2[nH]1] | cis-4-({7-bromo-2-[(2-methyl-1H-benzo[d]imidazol-6-yl)amino]quinazolin-8-yl}oxy)cyclohexanol |
| 19 | 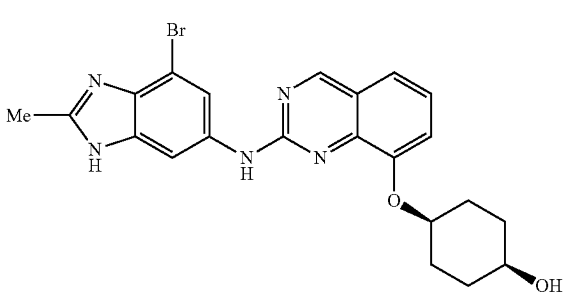 [SMILES: Cc1nc2c(Br)cc(Nc3ncc4cccc(O[C@H]5CC[C@@H](O)CC5)c4n3)cc2[nH]1] | cis-4-({2-[(4-bromo-2-methyl-1H-benzo[d]imidazol-6-yl)amino]quinazolin-8-yl}oxy)cyclohexanol |

TABLE 1-continued

| Ex. | Structure | Name |
|---|---|---|
| 20 | 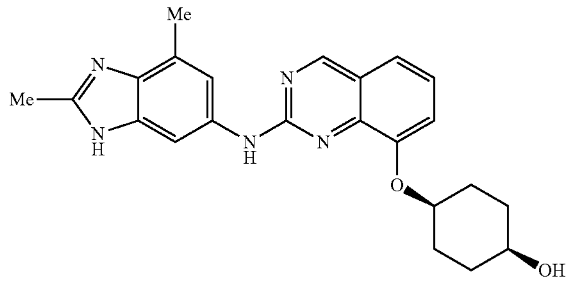 [SMILES: Cc1nc2c(C)cc(Nc3ncc4cccc(O[C@H]5CC[C@@H](O)CC5)c4n3)cc2[nH]1] | cis-4-({2-[(2,4-dimethyl-1H-benzo[d]imidazol-6-yl)amino]quinazolin-8-yl}oxy)cyclohexanol |
| 21 | 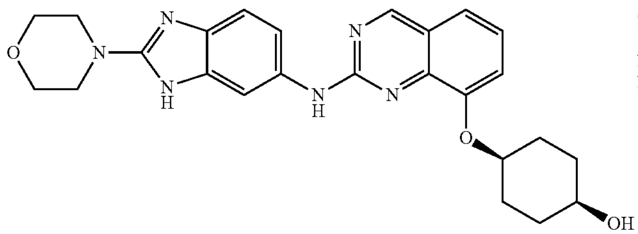 | cis-4-({2-[(2-morpholino-1H-benzo[d]imidazol-6-yl)amino]quinazolin-8-yl}oxy)cyclohexanol |
| 22 | 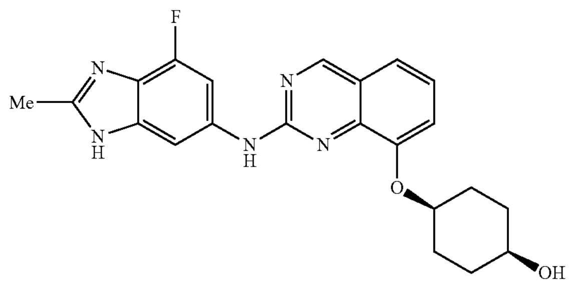 [SMILES: Cc1nc2c(F)cc(Nc3ncc4cccc(O[C@H]5CC[C@@H](O)CC5)c4n3)cc2[nH]1] | cis-4-({2-[(4-fluoro-2-methyl-1H-benzo[d]imidazol-6-yl)amino]quinazolin-8-yl}oxy)cyclohexanol |
| 23 | 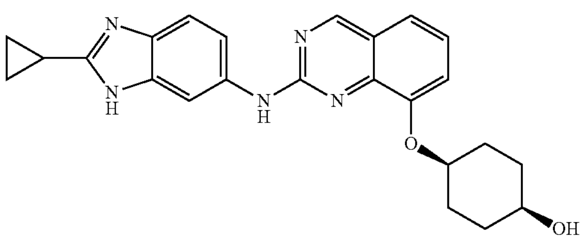 [SMILES: O[C@H]1CC[C@@H](Oc2cccc3cnc(Nc4ccc5nc(C6CC6)[nH]c5c4)nc23)CC1] | cis-4-({2-[(2-cyclopropyl-1H-benzo[d]imidazol-6-yl)amino]quinazolin-8-yl}oxy)cyclohexanol |
| 24 | 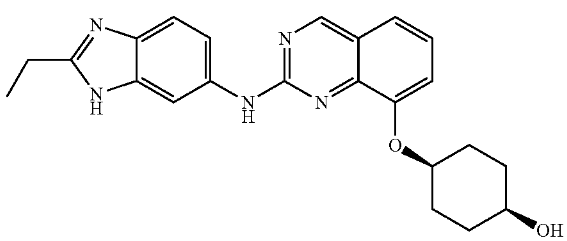 [SMILES: CCc1nc2ccc(Nc3ncc4cccc(O[C@H]5CC[C@@H](O)CC5)c4n3)cc2[nH]1] | cis-4-({2-[(2-ethyl-1H-benzo[d]imidazol-6-yl)amino]quinazolin-8-yl}oxy)cyclohexanol |
| 25 | 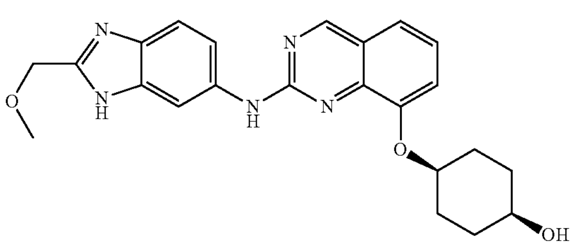 [SMILES: COCc1nc2ccc(Nc3ncc4cccc(O[C@H]5CC[C@@H](O)CC5)c4n3)cc2[nH]1] | cis-4-[(2-{[2-(methoxymethyl)-1H-benzo[d]imidazol-6-yl]amino}quinazolin-8-yl)oxy]cyclohexanol |

TABLE 1-continued

| Ex. | Structure | Name |
|---|---|---|
| 26 | 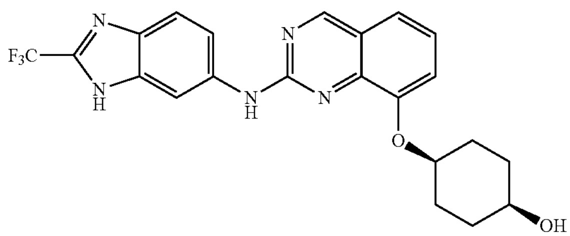 [SMILES: O[C@H]1CC[C@@H](Oc2cccc3cnc(Nc4ccc5nc(C(F)(F)F)[nH]c5c4)nc23)CC1] | cis-4-((2-{[2-(trifluoromethyl)-1H-benzo[d]imidazol-6-yl]amino}quinazolin-8-yl)oxy)cyclohexanol |
| 27 | 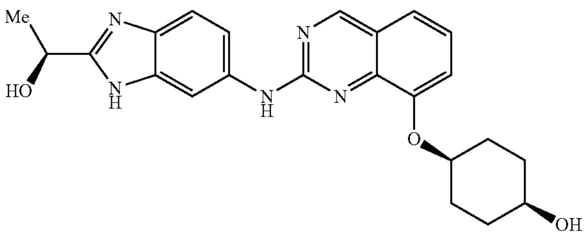 [SMILES: C[C@H](O)c1nc2ccc(Nc3ncc4cccc(O[C@H]5CC[C@@H](O)CC5)c4n3)cc2[nH]1] | cis-4-{[2-({2-[(S)-1-hydroxyethyl]-1H-benzo[d]imidazol-6-yl}amino)quinazolin-8-yl]oxy}cyclohexanol |
| 28 | 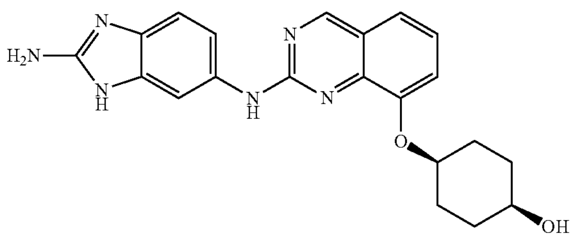 [SMILES: Nc1nc2ccc(Nc3ncc4cccc(O[C@H]5CC[C@@H](O)CC5)c4n3)cc2[nH]1] | cis-4-({2-[(2-amino-1H-benzo[d]imidazol-6-yl)amino]quinazolin-8-yl}oxy)cyclohexanol |
| 29 | 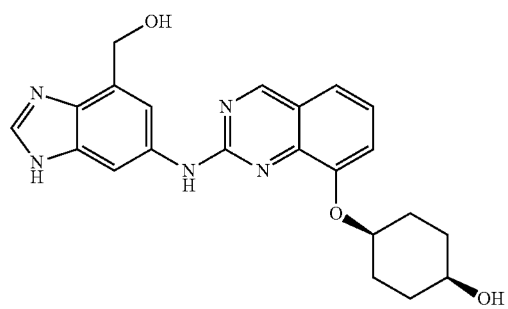 [SMILES: OCc1cc(Nc2ncc3cccc(O[C@H]4CC[C@@H](O)CC4)c3n2)cc2[nH]cnc12] | cis-4-[(2-{[4-(hydroxymethyl)-1H-benzo[d]imidazol-6-yl]amino}quinazolin-8-yl)oxy]cyclohexanol |
| 30 | 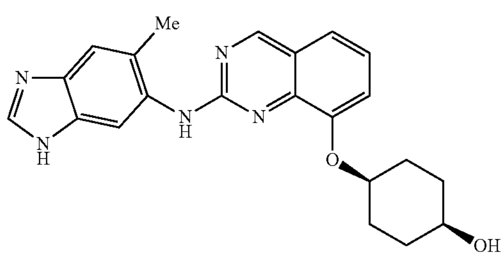 [SMILES: Cc1cc2nc[nH]c2cc1Nc1ncc2cccc(O[C@H]3CC[C@@H](O)CC3)c2n1] | cis-4-({2-[(5-methyl-1H-benzo[d]imidazol-6-yl)amino]quinazolin-8-yl}oxy)cyclohexanol |
| 31 | 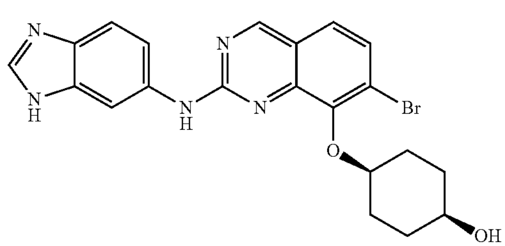 [SMILES: O[C@H]1CC[C@@H](Oc2c(Br)ccc3cnc(Nc4ccc5nc[nH]c5c4)nc23)CC1] | cis-4-({2-[(1H-benzo[d]imidazol)-6-yl)amino]-7-bromoquinazolin-8-yl}oxy)cyclohexanol |

TABLE 1-continued

| Ex. | Structure | Name |
|---|---|---|
| 32 | 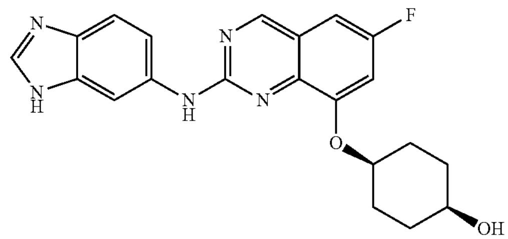 [SMILES: O[C@H]1CC[C@@H](Oc2cc(F)cc3cnc(Nc4ccc5nc[nH]c5c4)nc23)CC1] | cis-4-({2-[(1H-benzo[d]imidazol-6-yl)amino]-6-fluoroquinazolin-8-yl}oxy)cyclohexanol |
| 33 | 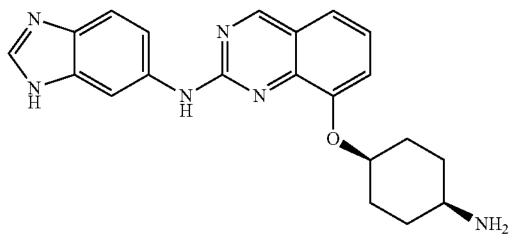 [SMILES: N[C@H]1CC[C@@H](Oc2cccc3cnc(Nc4ccc5nc[nH]c5c4)nc23)CC1] | 8-[(cis-4-aminocyclohexyl)oxy]-N-(1H-benzo[d]imidazol-6-yl)quinazolin-2-amine |
| 34 | 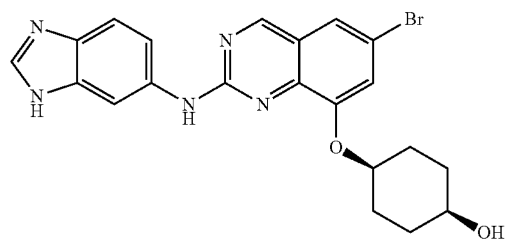 [SMILES: O[C@H]1CC[C@@H](Oc2cc(Br)cc3cnc(Nc4ccc5nc[nH]c5c4)nc23)CC1] | cis-4-({2-[(1H-benzo[d]imidazol-6-yl)amino]-6-bromoquinazolin-8-yl}oxy)cyclohexanol |
| 35 | 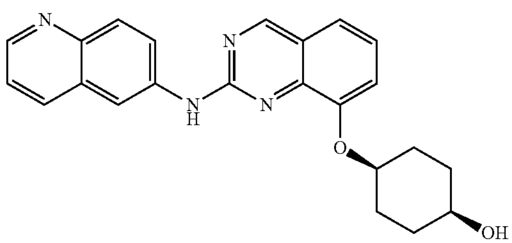 [SMILES: O[C@H]1CC[C@@H](Oc2cccc3cnc(Nc4ccc5ncccc5c4)nc23)CC1] | cis-4-{[2-(quinolin-6-ylamino)quinazolin-8-yl]oxy}cyclohexanol |
| 36 | 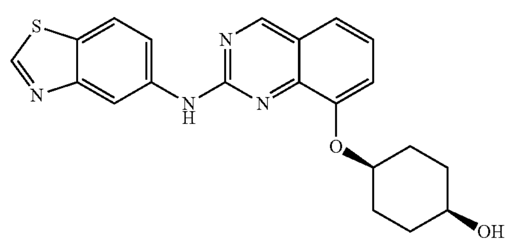 [SMILES: O[C@H]1CC[C@@H](Oc2cccc3cnc(Nc4ccc5scnc5c4)nc23)CC1] | cis-4-{[2-(benzo[d]thiazol-5-ylamino)quinazolin-8-yl]oxy}cyclohexanol |
| 37 | 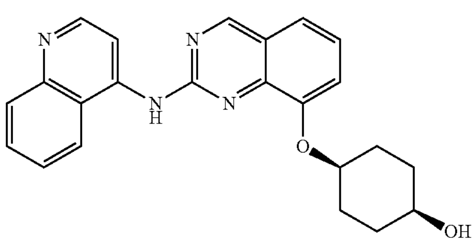 [SMILES: O[C@H]1CC[C@@H](Oc2cccc3cnc(Nc4ccnc5ccccc45)nc23)CC1] | cis-4-{[2-(quinolin-4-ylamino)quinazolin-8-yl]oxy}cyclohexanol |

TABLE 1-continued

| Ex. | Structure | Name |
|---|---|---|
| 38 | 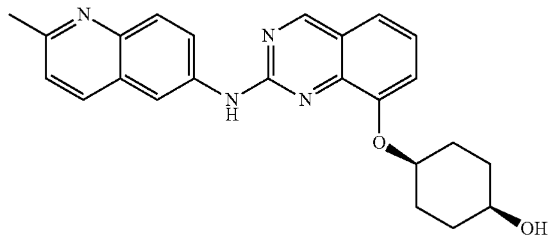 [SMILES: Cc1ccc2cc(Nc3ncc4cccc(O[C@H]5CC[C@@H](O)CC5)c4n3)ccc2n1] | cis-4-({2-[(2-methylquinolin-6-yl)amino]quinazolin-8-yl}oxy)cyclohexanol |
| 39 | 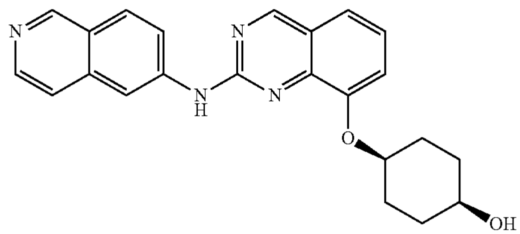 [SMILES: O[C@H]1CC[C@@H](Oc2cccc3cnc(Nc4ccc5cnccc5c4)nc23)CC1] | cis-4-{[2-(isoquinolin-6-ylamino)quinazolin-8-yl]oxy}cyclohexanol |
| 40 | 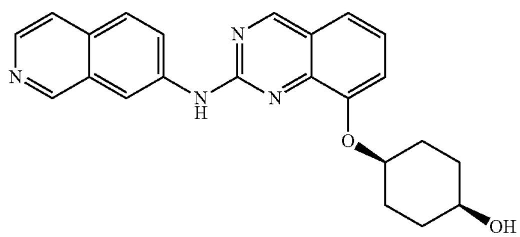 [SMILES: O[C@H]1CC[C@@H](Oc2cccc3cnc(Nc4ccc5ccncc5c4)nc23)CC1] | cis-4-{[2-(isoquinolin-7-ylamino)quinazolin-8-yl]oxy}cyclohexanol |
| 41 | 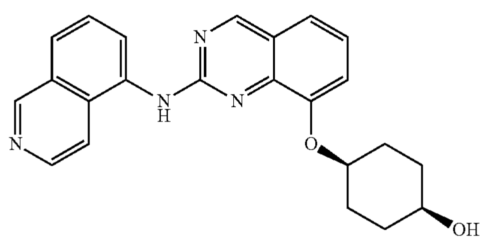 [SMILES: O[C@H]1CC[C@@H](Oc2cccc3cnc(Nc4cccc5cnccc45)nc23)CC1] | cis-4-{[2-(isoquinolin-5-ylamino)quinazolin-8-yl]oxy}cyclohexanol |
| 42 | 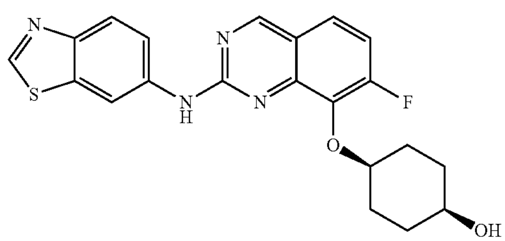 [SMILES: O[C@H]1CC[C@@H](Oc2c(F)ccc3cnc(Nc4ccc5ncsc5c4)nc23)CC1] | cis-4-{[2-(benzo[d]thiazol-6-ylamino)-7-fluoroquinazolin-8-yl]oxy}cyclohexanol |
| 43 | 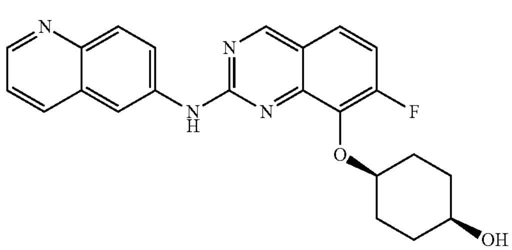 [SMILES: O[C@H]1CC[C@@H](Oc2c(F)ccc3cnc(Nc4ccc5ncccc5c4)nc23)CC1] | cis-4-{[7-fluoro-2-(quinolin-6-ylamino)quinazolin-8-yl]oxy}cyclohexanol |

TABLE 1-continued

| Ex. | Structure | Name |
|-----|-----------|------|
| 44 | 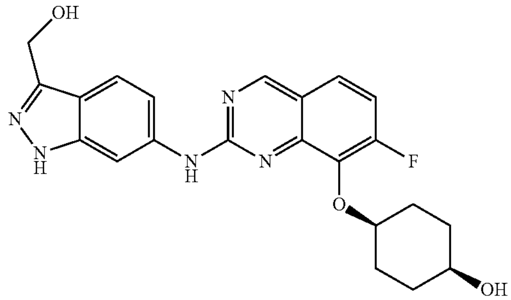 | cis-4-[(7-fluoro-2-{[3-(hydroxymethyl)-1H-indazol-6-yl]amino}quinazolin-8-yl)oxy]cyclohexanol |
| 45 | 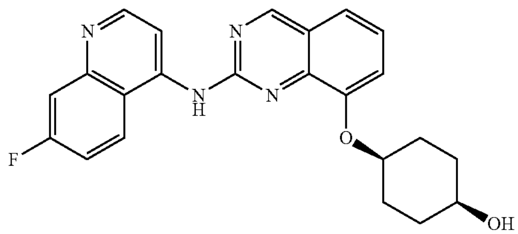 [SMILES: O[C@H]1CC[C@@H](Oc2cccc3cnc(Nc4ccnc5cc(F)ccc45)nc23)CC1] | cis-4-({2-[(7-fluoroquinolin-4-yl)amino]quinazolin-8-yl}oxy)cyclohexanol |
| 46 | 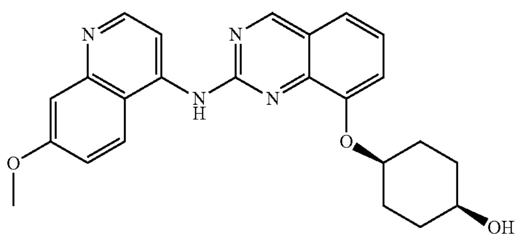 [SMILES: COc1ccc2c(Nc3ncc4cccc(O[C@H]5CC[C@@H](O)CC5)c4n3)ccnc2c1] | cis-4-({2-[(7-methoxyquinolin-4-yl)amino]quinazolin-8-yl}oxy)cyclohexanol |

TABLE 2

| Ex. | $^1$H-NMR δ (ppm) | LCMS m/z [M + H]$^+$ |
|-----|-------------------|----------------------|
| 2 | (DMSO-d6) δ 12.72 (s, 1H), 10.04 (s, 1H), 9.28 (s, 1H), 8.91-9.02 (m, 1H), 7.71 (d, J = 8.7 Hz, 1H), 7.46 (dd, J = 7.9, 1.2 Hz, 1H), 7.37-7.41 (m, 1H), 7.18-7.36 (m, 2H), 5.86 (s, 1H), 5.14 (t, J = 5.8 Hz, 1H), 4.91 (s, 1H), 4.73 (d, J = 5.8 Hz, 2H), 3.65-3.86 (m, 1H), 1.89-2.13 (m, 4H), 1.73-1.87 (m, 2H), 1.6-1.73 (m, 2H). | 406.0 |
| 3 | (DMSO-d6) δ 12.76 (s, 1H), 10.03 (s, 1H), 9.28 (s, 1H), 8.98 (s, 1H), 8.34 (s, 1H), 7.68 (d, J = 8.8 Hz, 1H), 7.23-7.5 (m, 3H), 5.91 (s, 1H), 4.86-4.99 (m, 1H), 3.65-3.82 (m, 3H), 2.20 (s, 6H), 1.58-2.10 (m, 8H). | 433.3 |
| 4 | (DMSO-d6) δ 12.63 (s, 1H), 10.02 (s, 1H), 9.29 (s, 1H), 8.53 (d, J = 1.6 Hz, 1H), 7.13-7.75 (m, 5H), 5.19 (t, J = 5.7 Hz, 1H), 4.75 (d, J = 5.2 Hz, 2H), 4.43-4.55 (m, 1H), 3.01-3.13 (m, 1H), 2.82-2.94 (m, 2H), 1.90-2.03 (m, 2H). | 377.2 |
| 5 | (DMSO-d6) δ 12.61 (s, 1H), 10.06 (s, 1H), 9.31 (s, 1H), 8.52 (s, 1H), 7.49-7.76 (m, 3H), 7.30 (t, J = 7.9 Hz, 1H), 7.15-7.22 (m, 1H), 5.26 (d, J = 5.6 Hz, 1H), 5.15-5.23 (m, 1H), 4.72-4.81 (m, 3H), 4.34-4.44 (m, 1H), 3.66-3.73 (m, 2H), 3.45 (s, 3H), 2.94-3.05 (m, 2H), 2.08-2.32 (m, 4H). | 483.3 |
| 6 | (DMSO-d6) δ 12.46 (s, 1H), 10.04 (s, 1H), 9.30 (s, 1H), 8.57 (s, 1H), 7.26-7.74 (m, 5H), 6.25 (dt, J = 5.6, 1.6 Hz, 1H), 6.11 (dt, J = 5.7, 1.6 Hz, 1H), 5.35-5.45 (m, 1H), 5.32 (d, J = 6.0 Hz, 1H), 5.13-5.21 (m, 1H), 4.74 (d, J = 5.8 Hz, 2H), 4.62-4.70 (m, 1H), 3.57-3.64 (m, 1H), 2.93-3.04 (m, 1H). | 390.3 |
| 7 | (DMSO-d6) δ 12.41 (s, 1H), 10.04 (s, 1H), 9.29 (s, 1H), 8.75 (s, 1H), 7.27-7.75 (m, 5H), 5.16 (t, J = 5.8 Hz, 1H), 5.09 (d, J = 4.2 Hz, 1H), 4.97-5.06 (m, 1H), 4.74 (d, J = 5.8 Hz, 2H), 4.19-4.30 (m, 1H), 1.77-2.13 (m, 6H). | 392.3 |
| 8 | (DMSO-d6) δ 12.74 (s, 1H), 10.06 (s, 1H), 9.26 (s, 1H), 8.95 (d, J = 1.6 Hz, 1H), 7.71 (d, J = 8.7 Hz, 1H), 7.40 (dd, J = 11.6, 2.6 Hz, 1H), 7.22-7.32 (m, 2H), 5.97 (s, 1H), 5.14 (t, J = 5.8 Hz, 1H), 4.96 (s, 1H), 4.73 (d, J = 5.8 Hz, 2H), 3.78 (s, 1H), 1.87-2.1 (m, 4H), 1.75-1.87 (m, 2H), 1.6-1.75 (m, 2H). | 424.3 |
| 9 | (CDCl3) δ 9.26 (s, 1H), 9.07 (s, 1H), 7.15-7.5 (m, 2H), 7.5-7.76 (m, 3H), 6.76 (dd, J = 8.7, 1.8 Hz, 1H), 5.29-5.37 (m, 1H), 4.90 (d, J = 3.4 Hz, 1H), 3.95-4.05 (m, 1H), 3.63-3.68 (m, 1H), 2.88-3.01 (m, 1H), 1.2-2.1 (m, 11H). | 420.4 |
| 10 | (DMSO-d6) δ 12.55 (s, 1H), 10.14 (s, 1H), 9.34 (s, 1H), 8.23 (s, 1H), 7.74 (d, J = 8.6 Hz, 1H), 7.5-7.65 (m, 3H), 5.18 (t, J = 5.8 Hz, 1H), 4.75 (d, J = 5.9 Hz, 2H), 4.49 (d, J = 3.3 Hz, 1H), 3.55-3.65 (m, 1H), 1.6-2.1 (m, 8H). | 486.2 |
| 11 | (DMSO-d6) δ 12.41-12.67 (m, 1H), 9.86-10.03 (m, 1H), 9.26 (s, 1H), 8.79 (br, 1H), 7.56-7.69 (m, 1H), 7.34-7.49 (m, 2H), 7.22-7.32 (m, 1H), 5.89 (br, 1H), 4.88 (br, 1H), 3.30 (s, 1H), 2.47 (br, 3H), 1.84-2.09 (m, 4H), 1.58-1.82 (m, 4H). | 424.2 |
| 12 | (DMSO-d6) δ 12.07-12.26 (m, 1H), 9.65-9.93 (m, 1H), 9.13-9.28 (m, 1H), 8.64-9.14 (m, 1H), 7.29-7.47 (m, 4H), 7.12-7.29 (m, 1H), 5.76-6.41 (m, 1H), 4.90 (s, 1H), 3.4-3.81 (m, 1H), 2.4-2.47 (m, 3H), 1.86-2.14 (m, 4H), 1.36-1.86 (m, 4H). | 390.3 |

TABLE 2-continued

| Ex. | ¹H-NMR δ (ppm) | LCMS m/z [M + H]⁺ |
|---|---|---|
| 13 | (DMSO-d6) δ 12.2-12.4 (m, 1H), 9.75-9.9 (m, 1H), 9.22 (s, 1H), 9.05 (br, 1H), 8.61 (br, 1H), 7.39-7.65 (m, 2H), 7.15-7.37 (m, 2H), 5.5-6.25 (m, 1H), 4.88 (br, 1H), 3.65-3.85 (m, 3H), 2.4-2.6 (m, 4H), 1.8-2.2 (m, 4H), 1.55-1.8 (m, 8H). | 459.3 |
| 14 | (DMSO-d6) δ 12.29 (br, 1H), 9.83 (br, 1H), 9.23 (s, 1H), 8.55-9.1 (m, 1H), 7.31-7.70 (m, 4H), 7.17-7.29 (m, 1H), 5.40-5.79 (m, 2H), 4.87 (br, 1H), 4.64 (br, 2H), 2.4-2.6 (m, 1H), 1.82-2.1 (m, 4H), 1.56-1.82 (m, 4H) | 406.4 |
| 15 | (DMSO-d6) δ 10.24 (s, 1H), 9.32 (d, J = 8.2 Hz, 2H), 9.20 (s, 1H), 7.91-8.06 (m, 2H), 7.51 (d, J = 7.7 Hz, 1H), 7.42-7.22 (m, 2H), 4.74 (br, 1H), 4.56 (br, 1H), 3.65 (br, 1H), 2.07 (q, J = 5.9 Hz, 2H), 1.5-1.89 (m, 6H). | 393.0 |
| 16 | (DMSO-d6) δ 10.24 (s, 1H), 9.31 (s, 1H), 9.01 (d, J = 1.9 Hz, 1H), 8.60 (s, 1H), 7.90 (dd, J = 8.8, 1.9 Hz, 1H), 7.72 (d, J = 8.7 Hz, 1H), 7.51 (d, J = 7.9 Hz, 1H), 7.38 (d, J = 7.5 Hz, 1H), 7.31 (t, J = 7.8 Hz, 1H), 4.73 (s, 1H), 4.54 (s, 1H), 3.54-3.73 (m, 1H), 1.95-2.15 (m, 2H), 1.51-1.88 (m, 6H). | 377.2 |
| 17 | (DMSO-d6) δ 12.01-12.53 (m, 1H), 9.75 (s, 1H), 9.19 (s, 1H), 7.90-8.57 (m, 2H), 7.71 (d, J = 8.7 Hz, 2H), 7.50 (d, J = 8.2 Hz, 2H), 7.18 (d, J = 8.2 Hz, 1H), 5.03 (s, 1H), 4.44 (s, 1H), 3.58 (s, 1H), 2.41 (s, 3H), 1.74-2.06 (m, 2H), 1.5-1.81 (m, 4H), 1.24-1.48 (m, 2H). | 390.4 |
| 18 | (DMSO-d6) δ 12.6 (br, 1H), 9.91 (s, 1H), 9.27 (s, 1H), 8.05 (d, J = 1.9 Hz, 1H), 7.64 (dd, J = 8.6, 2.0 Hz, 1H), 7.44-7.58 (m, 2H), 7.40 (d, J = 8.6 Hz, 1H), 5.15 (dt, J = 7.9, 4.0 Hz, 1H), 3.52-3.65 (m, 1H), 2.4-2.6 (m, 3H), 1.84-2.03 (m, 2H), 1.52-1.80 (m, 4H), 1.27-1.46 (m, 2H). | 470.1 |
| 19 | (DMSO-d6) δ 12.25-12.69 (m, 1H), 9.73-10.05 (m, 1H), 9.25 (d, J = 3.5 Hz, 1H), 8.49-9.05 (m, 1H), 7.65-7.79 (m, 1H), 7.44 (d, J = 8.0 Hz, 1H), 7.37 (d, J = 7.7 Hz, 1H), 7.24-7.31 (m, 1H), 5.68-5.99 (m, 1H), 4.88 (s, 1H), 3.77 (s, 1H), 2.4-2.6 (m, 3H), 1.84-2.10 (m, 4H), 1.61-1.83 (m, 4H). | 470.2 |
| 20 | (DMSO-d6) δ 9.74 (s, 1H), 9.21 (br, 1H), 8.77-8.90 (m, 1H), 7.41 (d, J = 7.9 Hz, 1H), 7.35 (d, J = 7.6 Hz, 1H), 7.23 (dd, J = 15.3, 7.5 Hz, 2H), 4.88 (s, 1H), 3.65 (s, 1H), 2.47 (s, 3H), 2.36 (s, 3H), 1.5-2.1 (m, 8H). | 404.4 |
| 21 | (DMSO-d6) δ 11.35 (s, 1H), 9.67 (s, 1H), 9.19 (s, 1H), 8.40 (s, 1H), 7.42 (dd, J = 10.6, 7.9 Hz, 2H), 7.33 (d, J = 7.8 Hz, 1H), 7.05-7.26 (m, 2H), 5.76 (s, 1H), 4.86 (s, 1H), 3.54-3.89 (m, 4H), 3.38-3.55 (m, 4H), 3.16 (t, J = 8.5 Hz, 1H), 1.88-2.10 (m, 4H), 1.46-1.76 (m, 4H). | 461.4 |
| 22 | (DMSO-d6) δ 12.19-12.77 (m, 1H), 9.69-10.10 (m, 1H), 9.25 (s, 1H), 8.31-8.85 (m, 1H), 7.41-7.48 (m, 1H), 7.34-7.42 (m, 2H), 7.23-7.32 (m, 1H), 5.84 (s, 1H), 4.88 (s, 1H), 3.76 (s, 1H), 2.45 (s, 3H), 1.84-2.09 (m, 6H), 1.61-1.82 (m, 2H). | 408.2 |
| 23 | (DMSO-d6) δ 12.01-12.21 (m, 1H), 9.61-9.94 (m, 1H), 9.21 (d, J = 3.7 Hz, 1H), 8.57-8.97 (m, 1H), 7.05-7.51 (m, 5H), 5.71-6.03 (m, 1H), 4.89 (s, 1H), 3.39-3.86 (m, 1H), 1.87-2.14 (m, 4H), 1.52-1.83 (m, 4H), 1.18-1.34 (m, 1H), 0.91-1.11 (m, 4H). | 416.2 |
| 24 | (DMSO-d6) δ 11.98-12.22 (m, 1H), 9.82 (s, 1H), 9.22 (s, 1H), 8.65-9.09 (m, 1H), 7.3-7.4 (m, 4H), 7.24 (t, J = 7.8 Hz, 1H), 5.69-6.32 (m, 1H), 4.89 (s, 1H), 3.4-3.8 (m, 1H), 2.79 (q, J = 7.6 Hz, 2H), 1.86-2.19 (m, 4H), 1.55-1.86 (m, 4H), 1.32 (t, J = 7.6 Hz, 3H). | 404.3 |
| 25 | (DMSO-d6) δ 12.49 (s, 1H), 9.75-9.9 (m, 1H), 9.23 (s, 1H), 8.65-9.1 (m, 1H), 7.61-7.20 (m, 5H), 5.55-6.0 (m, 1H), 4.88 (s, 1H), 4.58 (d, J = 8.4 Hz, 2H), 3.4-3.8 (m, 1H), 3.34-3.38 (m, 3H), 1.58-2.13 (m, 8H). | 420.5 |
| 26 | (DMSO-d6) δ 13.7-13.85 (m, 1H), 9.95-10.16 (m, 1H), 9.25-9.33 (m, 1H), 8.78-9.06 (m, 1H), 7.5-8.12 (m, 2H), 7.22-7.5 (m, 3H), 6.18 (s, 1H), 4.87-4.97 (m, 1H), 3.7-3.86 (m, 1H), 1.56-2.15 (m, 8H). | 444.4 |
| 27 | (DMSO-d6) δ 12.18 (s, 1H), 9.80 (d, J = 4.1 Hz, 1H), 9.22 (s, 1H), 9.06-8.40 (m, 1H), 7.37-7.70 (m, 2H), 7.34 (d, J = 7.6 Hz, 1H), 7.24 (t, J = 7.8 Hz, 1H), 5.65-6.15 (m, 1H), 5.53 (s, 1H), 4.74-4.95 (m, 2H), 3.45-3.79 (m, 1H), 1.84-2.19 (m, 4H), 1.56-1.82 (m, 4H), 1.50 (d, J = 6.6 Hz, 3H). | 420.0 |
| 28 | (DMSO-d6) δ 9.62 (s, 1H), 9.18 (s, 1H), 8.24-8.37 (m, 1H), 8.21 (s, 1H), 7.41 (dd, J = 7.9, 1.3 Hz, 2H), 7.32 (dd, J = 8.0, 1.3 Hz, 1H), 7.21 (t, J = 7.8 Hz, 1H), 7.06 (d, J = 8.4 Hz, 1H), 6.26 (s, 2H), 4.84 (s, 1H), 3.47-3.75 (m, 1H), 1.79-2.08 (m, 4H), 1.5-1.81 (m, 4H). | 391.4 |
| 29 | (DMSO-d6) δ 12.40 (br, 1H), 9.84 (s, 1H), 9.23 (s, 1H), 8.99 (s, 1H), 8.08 (s, 1H), 7.39-7.46 (m, 2H), 7.32-7.37 (m, 1H), 7.25 (t, J = 7.8 Hz, 1H), 5.87 (s, 1H), 5.20 (s, 1H), 4.75-4.95 (m, 3H), 3.66 (s, 1H), 1.86-2.11 (m, 4H), 1.84-1.53 (m, 4H) | 406.2 |
| 30 | (DMSO-d6) δ 9.22 (s, 1H), 8.72 (s, 1H), 8.42 (s, 1H), 8.26 (s, 1H), 7.39-7.50 (m, 2H), 7.30 (dd, J = 7.9, 1.4 Hz, 1H), 7.22 (t, J = 7.8 Hz, 1H), 4.71 (d, J = 4.4 Hz, 1H), 4.09 (s, 1H), 3.57-3.65 (m, 1H), 2.43 (s, 3H), 1.8-1.93 (m, 2H), 1.68-1.81 (m, 2H), 1.46-1.64 (m, 4H). | 390.2 |
| 31 | (DMSO-d6) δ 12.06-12.47 (m, 1H), 9.72-10.11 (m, 1H), 9.1-9.36 (m, 1H), 7.99-8.4 (m, 2H), 7.65 (t, J = 9.3 Hz, 1H), 7.33-7.58 (m, 3H), 5.18 (s, 1H), 4.35-4.52 (m, 1H), 3.43-3.66 (m, 1H), 1.85-2.13 (m, 2H), 1.55-1.8 (m, 4H), 1.25-1.4 (m, 2H) | 454.1 |
| 32 | (DMSO-d6) δ 9.92 (s, 1H), 9.21 (s, 1H), 8.92 (s, 1H), 8.14 (s, 1H), 7.55 (d, J = 7.5 Hz, 2H), 7.35 (d, J = 11.3 Hz, 1H), 7.16-7.28 (m, 2H), 4.92 (s, 1H), 3.51-3.78 (m, 1H), 1.86-2.09 (m, 6H), 1.51-1.87 (m, 2H) | 394.3 |
| 33 | (DMSO-d6) δ 9.89 (s, 1H), 9.12-9.38 (m, 2H), 8.00 (s, 1H), 7.52 (d, J = 8.6 Hz, 1H), 7.41 (dd, J = 7.9, 1.2 Hz, 1H), 7.35-7.39 (m, 1H), 7.2-7.33 (m, 3H), 4.99 (s, 1H), 2.96 (s, 1H), 1.93-2.02 (m, 2H), 1.84-1.93 (m, 2H), 1.6-1.78 (m, 4H) | 375.2 |
| 34 | (DMSO-d6) δ 12.43 (s, 1H), 10.03 (s, 1H), 9.20 (m, 1H), 8.69-9.10 (m, 1H), 8.12 (s, 1H), 7.68 (d, J = 1.9 Hz, 1H), 7.4-7.65 (m, 3H), 5.80 (br, 1H), 4.93 (s, 1H), 3.48-3.81 (m, 1H), 1.84-2.13 (m, 4H), 1.52-1.81 (m, 4H) | 454.0 |
| 35 | (DMSO-d6) δ 10.28 (s, 1H), 9.33 (s, 1H), 9.00 (d, J = 2.5 Hz, 1H), 8.73 (dd, J = 4.3, 1.7 Hz, 1H), 8.11-8.36 (m, 2H), 7.98 (d, J = 9.1 Hz, 1H), 7.16-7.62 (m, 4H), 4.67-4.88 (m, 1H), 4.64 (s, 1H), 3.56-3.77 (m, 1H), 1.97-2.22 (m, 2H), 1.72-1.91 (m, 4H), 1.58-1.72 (m, 2H). | 387.2 |
| 36 | (DMSO-d6) δ 10.36 (s, 1H), 9.38 (s, 1H), 9.35 (s, 1H), 8.95-9.05 (m, 1H), 8.14-8.26 (m, 1H), 8.09 (d, J = 8.8 Hz, 1H), 7.53 (dd, J = 8.0, 1.3 Hz, 1H), 7.42 (dd, J = 7.9, 1.4 Hz, 1H), 7.33 (t, J = 7.8 Hz, 1H), 4.71-4.88 (m, 1H), 3.58-3.69 (m, 1H), 1.95-2.12 (m, 2H), 1.78-1.94 (m, 2H), 1.60-1.78 (m, 4H). | 393.1 |
| 37 | (DMSO-d6) δ 10.17 (s, 1H), 9.46 (s, 1H), 9.15 (d, J = 5.3 Hz, 1H), 8.87 (d, J = 5.2 Hz, 1H), 8.66 (d, J = 8.5 Hz, 1H), 7.98 (d, J = 8.4 Hz, 1H), 7.74 (t, J = 7.6 Hz, 1H), 7.49-7.67 (m, 2H), 7.31-7.49 (m, 2H), 4.74-4.88 (m, 1H), 4.68 (s, 1H), 3.51-3.74 (m, 1H), 1.92-2.10 (m, 2H), 1.74-1.90 (m, 2H), 1.49-1.76 (m, 4H). | 387.0 |
| 38 | (DMSO-d6) δ 10.20 (s, 1H), 9.31 (s, 1H), 8.91 (d, J = 2.4 Hz, 1H), 8.21 (dd, J = 9.1, 2.4 Hz, 1H), 8.16 (d, J = 8.4 Hz, 1H), 7.88 (d, J = 9.1 Hz, 1H), 7.50 (dd, J = 7.9, 1.3 Hz, 1H), 7.21-7.46 (m, 3H), 4.69-4.83 (m, 1H), 4.63 (d, J = 3.4 Hz, 1H), 3.61-3.74 (m, 1H), 2.62 (s, 3H), 2.03-2.14 (m, 2H), 1.58-1.90 (m, 6H). | 401.2 |

TABLE 2-continued

| Ex. | $^1$H-NMR δ (ppm) | LCMS m/z [M + H]$^+$ |
|---|---|---|
| 39 | (DMSO-d6) δ 10.41 (s, 1H), 9.36 (s, 1H), 9.11 (s, 1H), 9.06 (d, J = 1.8 Hz, 1H), 8.38 (d, J = 5.8 Hz, 1H), 7.95-8.12 (m, 2H), 7.72 (d, J = 5.8 Hz, 1H), 7.53 (dd, J = 7.8, 1.4 Hz, 1H), 7.30-7.46 (m, 2H), 4.71-4.82 (m, 1H), 4.63-4.71 (m, 1H), 3.61-3.76 (m, 1H), 2.01-2.18 (m, 2H), 1.72-1.89 (m, 2H), 1.63-1.73 (m, 2H), 1.46-1.62 (m, 2H). | 387.3 |
| 40 | (DMSO-d6) δ 10.35 (s, 1H), 9.34 (s, 1H), 9.22 (s, 1H), 9.19 (s, 1H), 8.36 (d, J = 5.6 Hz, 1H), 8.13-8.24 (m, 1H), 7.93 (d, J = 8.9 Hz, 1H), 7.72 (d, J = 5.7 Hz, 1H), 7.52 (d, J = 7.8 Hz, 1H), 7.25-7.45 (m, 2H), 4.67-4.81 (m, 1H), 4.60 (s, 1H), 3.61-3.75 (m, 1H), 2.01-2.20 (m, 2H), 1.71-1.91 (m, 4H), 1.60-1.72 (m, 2H). | 387.1 |
| 41 | (DMSO-d6) δ 9.88 (s, 1H), 9.33 (s, 1H), 9.30 (s, 1H), 8.85 (d, J = 7.6 Hz, 1H), 8.49 (d, J = 6.0 Hz, 1H), 8.20 (d, J = 6.1 Hz, 1H), 7.86 (d, J = 8.1 Hz, 1H), 7.77 (t, J = 7.9 Hz, 1H), 7.52 (dd, J = 7.6, 1.6 Hz, 1H), 7.22-7.36 (m, 2H), 4.49-4.70 (m, 2H), 3.52-3.68 (m, 1H), 1.80-1.95 (m, 2H), 1.61-1.78 (m, 2H), 1.46-1.61 (m, 4H). | 387.1 |
| 42 | (DMSO-d6) δ 10.37 (s, 1H), 9.33 (s, 1H), 9.24 (s, 1H), 9.19-9.22 (m, 1H), 8.03 (d, J = 8.8 Hz, 1H), 7.87 (dd, J = 8.9, 2.1 Hz, 1H), 7.75 (dd, J = 8.8, 5.5 Hz, 1H), 7.35 (dd, J = 10.5, 8.8 Hz, 1H), 4.67-4.84 (m, 1H), 4.51 (d, J = 3.6 Hz, 1H), 3.50-3.70 (m, 1H), 1.90-2.11 (m, 2H), 1.59-1.87 (m, 4H), 1.42-1.61 (m, 2H). | 411.1 |
| 43 | (DMSO-d6) δ 10.39 (s, 1H), 9.35 (s, 1H), 8.65-8.86 (m, 2H), 8.25 (d, J = 8.1 Hz, 1H), 8.19 (dd, J = 9.2, 2.4 Hz, 1H), 7.97 (d, J = 9.1 Hz, 1H), 7.76 (dd, J = 8.8, 5.5 Hz, 1H), 7.49 (dd, J = 8.3, 4.2 Hz, 1H), 7.37 (dd, J = 10.6, 8.8 Hz, 1H), 4.71-4.93 (m, 1H), 4.52 (d, J = 3.5 Hz, 1H), 3.49-3.70 (m, 1H), 1.89-2.16 (m, 2H), 1.59-1.84 (m, 4H), 1.39-1.56 (m, 2H). | 405.2 |
| 44 | (DMSO-d6) δ 12.52 (s, 1H), 10.12 (s, 1H), 9.30 (s, 1H), 8.35 (s, 1H), 7.65-7.81 (m, 2H), 7.58 (d, J = 8.3 Hz, 1H), 7.32 (dd, J = 10.7, 8.8 Hz, 1H), 5.16 (t, J = 5.8 Hz, 1H), 4.81-4.92 (m, 1H), 4.75 (d, J = 5.7 Hz, 2H), 4.70 (d, J = 3.7 Hz, 1H), 3.50-3.65 (m, 1H), 1.92-2.09 (m, 2H), 1.71-1.83 (m, 2H), 1.59-1.72 (m, 2H), 1.44-1.60 (m, 2H). | 424.0 |
| 45 | (DMSO-d6) δ 10.31 (s, 1H), 9.46 (s, 1H), 9.14 (d, J = 5.3 Hz, 1H), 8.88 (d, J = 5.3 Hz, 1H), 8.76 (t, J = 7.7 Hz, 1H), 7.69 (d, J = 9.7 Hz, 1H), 7.58 (d, J = 7.2 Hz, 1H), 7.34-7.54 (m, 3H), 4.75-4.86 (m, 1H), 4.70 (d, J = 3.6 Hz, 1H), 3.57-3.73 (m, 1H), 1.93-2.13 (m, 2H), 1.74-1.90 (m, 2H), 1.56-1.74 (m, 4H). | 405.3 |
| 46 | (DMSO-d6) δ 10.53 (s, 1H), 9.50 (s, 1H), 9.15 (br, 1H), 8.83 (d, J = 5.7 Hz, 1H), 8.70 (d, J = 9.6 Hz, 1H), 7.61 (d, J = 6.2 Hz, 1H), 7.42-7.53 (m, 2H), 7.37 (d, J = 2.3 Hz, 1H), 7.30 (d, J = 9.3 Hz, 1H), 4.79-4.88 (m, 1H), 4.75 (d, J = 3.6 Hz, 1H), 3.95 (s, 3H), 3.58-3.74 (m, 1H), 1.93-2.12 (m, 2H), 1.75-1.91 (m, 2H), 1.59-1.75 (m, 4H). | 417.0 |

Example 47

Production of cis-4-({2-[(1H-benzo[d]imidazol-6-yl)amino]quinazolyn-8-yl}oxy)cyclohexanol hydrochloride

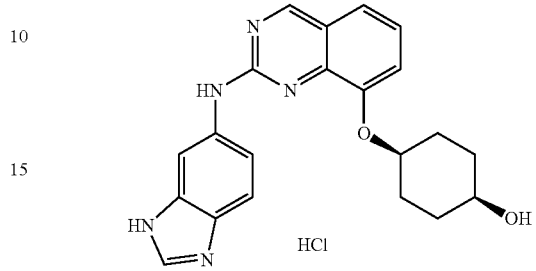

To the compound of Example 1 (19.3 g, 51.4 mmol), 0.2 M hydrochloric acid-ethanol (273 mL, 51.4 mmol) was added, and the mixture was stirred at 35-50° C. for 24 hours. After the mixture was cooled to room temperature, a precipitated product was filtered, washed with a small amount of ethanol, and dried to give the title compound (18.0 g).
$^1$H-NMR (DMSO-d$_6$) δ(ppm): 10.34 (s, 1H), 9.48 (s, 1H), 9.33 (s, 1H), 8.91 (d, J=1.9 Hz, 1H), 8.13 (dd, J=9.1, 1.9 Hz, 1H), 7.82 (d, J=9.0 Hz, 1H), 7.50 (dd, J=8.0, 1.2 Hz, 1H), 7.42 (dd, J=8.0, 0.9 Hz, 1H), 7.34 (t, J=7.8 Hz, 1H), 4.78-4.95 (m, 1H), 3.69-3.85 (m, 1H), 1.96-2.11 (m, 2H), 1.81-1.96 (m, 2H), 1.60-1.83 (m, 4H); LC-MS (m/z) 376.0 [M+H]$^+$; melting point: 241.6° C. (onset).

Test Example 1

Evaluation of Inhibitory Activity Against Wnt/β-Catenin Signaling

Evaluation of inhibitory activity of the compounds of the present invention against the Wnt/β-catenin signaling pathway was performed by evaluating the inhibitory activity of the compounds of the present invention against the Wnt/β-catenin signaling pathway activated by the Wnt-3a ligand using a commercially available TCF-luciferase reporter gene assay system.
(Culture of Cells to be Used)
In a T75 flask, HEK 293 cells (ATCC No. CRL-1573) were added to a DMEM medium (manufactured by NACALAI TESQUE, INC., No. 08459-35) supplemented with 10% FBS (AusGeneX PTY LTD.) and 1% Penicillin/Streptomycin (NACALAI TESQUE, INC.). The cells in the flask were cultured in a 5% CO$_2$ incubator.
(Transfection of Reporter Gene and Addition of the Compound to be Tested)
The cultured HEK 293 cells were diluted with a DMEM medium supplemented with only 10% FBS so as to have a cell concentration of 2×10$^5$ cells/mL, and 100 µL each of the diluted cells were seeded into respective wells of 96-well plates (PerkinElmer Inc., ViewPlate No. 6005181), followed by culturing overnight in the 5% CO$_2$ incubator. To an OptiMEM medium (Invitrogen® No. 11058), pGL4.49 [luc2p/TCF-LEF-RE/Hygro] plasmid DNA (Promega Corporation) and FuGENE® HD (Promega No. E2691) were added so as to have concentrations of 1 µg/mL and 3 µg/mL, respectively, to prepare a transfection solution as described in the protocol attached to the reagent. To the respective wells containing the HEK 293 cells cultured overnight, 100 µL each of the transfection solution was added gently, followed by culturing overnight in the 5% $CO_2$ incubator to perform transfection.

To a DMEM medium, 0.5% charcoal/dextran treated Fetal Bovine Serum (Thermo Scientific No. SH30068.02) and LiCl (Sigma-Aldrich No. L9650) were added to prepare a LiCl-containing medium (final concentration of LiCl: 10 mM). The medium in the respective wells of the HEK 293 cells cultured overnight and transfected with a reporter gene was removed by decantation. The LiCl-containing medium (90 µL) was added gently to each well, followed by culturing overnight in the 5% $CO_2$ incubator.

A DMSO stock solution of the compound to be tested was diluted 100-fold with a LiCl-containing medium so as to prepare a solution of the compound to be tested, which is 10 times the test concentration. Further, Recombinant Mouse Wnt-3a (R&D Systems, Inc. #1324-WN) was dissolved in a 0.1% BSA-PBA solution so as to have a concentration of 40 µg/mL, and the resultant solution was diluted with a LiCl-containing medium so as to have a concentration of 100 ng/mL, to prepare a Wnt-3a solution. To each well of the HEK 293 cells cultured overnight in the LiCl-containing medium, 10 µL each of the solution of the compound to be tested was added, followed by culturing in the 5% $CO_2$ incubator for 2 hours (the final concentration of the compound to be tested: 3-0.03 µM). Thereafter, 10 µL each of the Wnt-3a solution was added to the respective wells, followed by further culturing for 5 hours.

(Measurement of Luciferase Activity)

Using ONE-Glo™ Luciferase Assay System (Promega Corporation, No. E6110), the luciferase activity of the cells in the wells was measured by a microplate reader (Synergy H1, BioTek Instruments, Inc.) An $IC_{50}$ value was calculated from the luminescence intensity of each compound concentration, supposing that the luminescence intensity of a group with no addition of the compound and with Wnt-3a stimulation was 100%, and that the luminescence intensity of a group with no addition of the compound and with no Wnt-3a stimulation was 0%.

(Evaluation Results)

The compounds of the present invention exhibited potent inhibitory activity in the TCF-luciferase reporter gene assay. The inhibitory activity of representative compounds of the present invention in the TCF-luciferase reporter gene assay is shown in Table 3. Regarding the inhibitory activity in the TCF-luciferase reporter gene assay, those having an $IC_{50}$ value of less than 0.3 µM are denoted with *, those having an $IC_{50}$ value of 0.3 µM or more and less than 1 µM are denoted with , and those having an $IC_{50}$ value of 1 µM or more and less than 3 µM are denoted with *.

TABLE 3

| Compound to be tested (Ex. No.) | Inhibitory activity against the Wnt/β-catenin signaling pathway |
|---|---|
| 1 | *** |
| 13 | *** |
| 14 | ** |
| 17 | ** |
| 18 | ** |
| 19 | * |
| 20 | ** |
| 25 | ** |
| 26 | * |
| 27 | ** |
| 29 | *** |
| 30 | ** |

TABLE 3-continued

| Compound to be tested (Ex. No.) | Inhibitory activity against the Wnt/β-catenin signaling pathway |
|---|---|
| 31 | *** |
| 32 | ** |
| 35 | ** |
| 36 | *** |
| 37 | *** |
| 38 | ** |
| 39 | ** |
| 40 | * |
| 41 | ** |
| 42 | *** |
| 43 | *** |
| 44 | *** |
| 45 | ** |
| 46 | ** |

The results demonstrate that the compounds (I) of the present invention have potent inhibitory activity against the Wnt/β-catenin signaling pathway.

Test Example 2

Study of Changes in Expression Levels of Genes Downstream of the Wnt/β-Catenin Signaling Effects of the compound of the present invention on Wnt/β-catenin signaling activity were studied using the real-time PCR method as well as using as an indicator changes in expression levels of target genes of the Wnt/β-catenin signaling pathway.

(Culture of Cells to be Used)

To a RPMI 1640 medium (NACALAI TESQUE, INC.), 10% FBS (AusGeneX PTY LTD.) and 1% Penicillin/Streptomycin (NACALAI TESQUE, INC.) were added to prepare a cell culture medium (hereinafter referred to as medium 1). In a T75 flask, HCT116 cells (ATCC No. CCL-247) were added to the medium 1. The cells in the flask were cultured in the 5% $CO_2$ incubator.

(Addition of the Compound to be Tested)

The cultured HCT116 cells were diluted with the medium 1 so as to have a cell concentration of $1.1 \times 10^5$ cells/mL. Into the T75 flask, 13.5 mL of the diluted cells was seeded, followed by culturing overnight in the 5% $CO_2$ incubator. Next day, to the cell solution, 1.5 mL each of solutions of the compound to be tested obtained by diluting 10 and 3 mM DMSO stock solutions of the compound to be tested 100-fold with the medium 1 were added (final concentrations of the compound to be tested: 10 and 3 µM), followed by culturing in the 5% $CO_2$ incubator for 24 hours.

(Extraction of Total RNA and Preparation of Reverse Transcription Reaction Solution)

Culture supernatant was centrifuged, and suspending cells were recovered as pellets. The pellets and cells attached to the inside of the T75 flask were combined, and total RNA was recovered using a RNeasy Plus Mini Kit (Qiagen No. 74134) and QIA shredder (Qiagen No. 79654) as described in the protocol attached to the kit. Total RNA concentration was measured by a microspectrophotometer (Thermo Fisher Scientific Inc., Nano Drop ND-1000). Reverse transcription reaction of 1 µg of total RNA was performed using ReverTra Ace® qPCR RT Master Mix (TOYOBO CO., LTD. No. FSQ-201) as described in the protocol attached to the reagent, to prepare a reverse transcription reaction solution.

(Quantification of Genes Downstream of the Wnt Signaling by Quantitative RT-PCR Method)

To 1 μL of the reverse transcription reaction solution, 10 μL of TaqMan® Universal PCR Master Mix (Applied Biosystems, No. 4304437), 1 μL each of TaqMan gene expression assays for each gene (Applied Biosystems) (refer to the following Table 4), and sterilized water (8 μL) were added to have a volume of 20 μL, and then real-time PCR was performed using a real-time thermal cycler (Applied Biosystems, PRISM 7300 Sequence Detection system). The PCR reaction was performed in the following manner: Using 96-well plates, after incubation at 50° C. for 2 min. and at 95° C. for 10 min., 40 cycles of warming at 95° C. for 15 sec. and at 60° C. for 1 min., which serves as one cycle, were repeated. The results were calculated as the expression ratio of the target gene to the endogenous control gene (β-Actin) by the comparative Ct method using a DMSO group as a reference.

TABLE 4

| Gene Name | Gene Expression Assays |
| --- | --- |
| AXIN2 | Hs00610344_m1 |
| MYC (c-MYC) | Hs00153408_m1 |
| ACBT (β-Actin) | Hs99999903_m1 |

Figure 2:
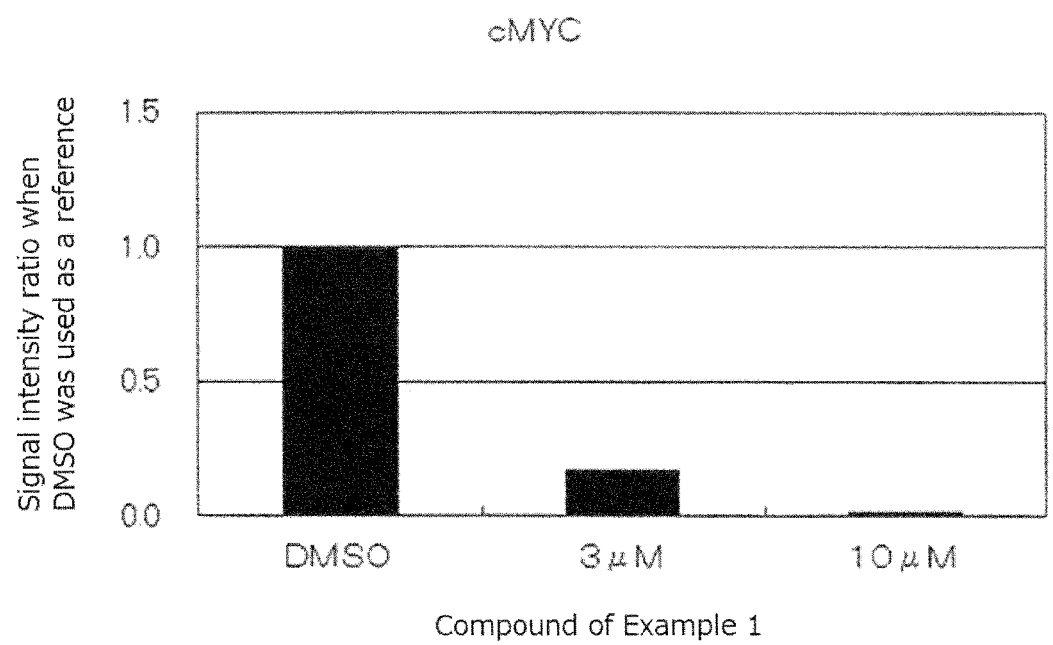
FIG. 2 shows that the compound of Example 1 inhibits c-MYC gene expression in HCT116 colorectal cancer cells in a concentration-dependent manner (Text Example 2).

As shown in FIGS. 1 and 2, the compounds of Example 1 inhibited the expression of AXIN2 and c-MYC that are Wnt/β-catenin signaling target genes in a concentration-dependent manner. As seen from the above, inhibition of the activity of the Wnt/β-catenin-signaling pathway by the compound of the present invention was able to be confirmed at the expression levels of the target genes.

Test Example 3

Study of Changes in Expression Levels of Target Proteins of the Wnt/β-Catenin Signaling Pathway Expression levels of target proteins of the Wnt/β-catenin signaling pathway was analyzed by western blotting method, and effects of the compound of the present invention on Wnt/β-catenin signaling activity were studied by using a change of these levels as an indicator.
(Addition of the Compound to be Tested)
HCT116 cells cultured in the same manner as in Test Example 2 were diluted with the medium 1 so as to have a cell concentration of $5 \times 10^5$ cells/mL, and 5 mL of the diluted cells were seeded into T25 flasks, followed by culturing overnight in the 5% $CO_2$ incubator. Next day, solutions of the compound to be tested obtained by diluting 10 and 3 mM DMSO stock solutions of the compound to be tested 100-fold with the medium 1 were added to each flask so that the amount of the solution in the flask was one tenth of the amount of the final solution (final concentrations of the compound to be tested: 10 and 3 μM). Thereafter, the cells in the flasks were cultured for 24 hours in the 5% $CO_2$ incubator.
(Extraction of Proteins)
Culture supernatant was centrifuged, and suspending cells were recovered as pellets. The cells attached to the flasks were carefully scraped using a rubber policeman in ice-cold PBS followed by centrifugation to recover the cells as pellets. These pellets were combined, washed twice with ice-cold PBS, and 50 μL of a lysis buffer [obtained by adding 5% phosphatase inhibitors (Active motif, Inc., Universal Magnetic Co-IP Kit #54002), 1% Deacetylase Inhibitor (same as above) and 1 mM phenylmethylsulfonyl fluoride (PMSF) to Whole Cell Lysis Buffer (same as above)] was added thereto. The mixture was gently stirred and then left to stand on ice for 30 minutes. Supernatant was recovered by centrifugal operation (15,000 rpm, 10 min.) and amounts of proteins were determined. An amount corresponding to 50 μg of protein was weighed from the supernatant, and mixed with a SDS sample buffer. The resultant mixture was reacted at 95° C. for 5 min. followed by denaturation of the protein to give a sample solution. The sample solution was applied to respective wells of 4-20% gradient acrylamide gel (COSMO BIO co., ltd., No. 414879) and then electrophoresis was performed. Thereafter, using iBlot gel transfer system (Life Technologies Co.), the proteins in the gel were transcribed onto a PVDF membrane.
(Detection of AXIN2, c-MYC and β-Actin)
The transcribed PVDF membrane was subjected to blocking treatment with 2% ECL Prime Blocking Reagent (GE Healthcare Co.). Then, the proteins were reacted overnight at 4° C. using as a primary antibody anti-AXIN2 rabbit antibody (Cell Signaling Co., No. 2151), anti-c-MYC rabbit antibody (Cell Signaling Co., No. 5605) or anti-β-Actin mouse antibody (Abeam plc., No. ab6276). Unreacted primary antibodies were washed with TBST buffer (10 mM Tris-HCl (pH 7.5), 150 mM NaCl, and 0.1% Tween 20). Thereafter, the proteins were reacted at room temperature for one hour in TBST buffer supplemented with 2% ECL Prime Blocking Reagent, using as a secondary antibody HRP-labeled Anti-Rabbit IgG Goat Antibody (Santa Cruz Biotechnology, Inc., No. sc2004) or HRP-labeled Anti-mouse IgG Goat Antibody (Zymed Laboratories, Inc., No. 62-6520). After unreacted secondary antibodies were washed with TBST buffer, the proteins were reacted using Chem-Lumi One Super (NACALAI TESQUE, INC.) as described in the attached protocol. Thereafter, using a CCD camera (GE Healthcare Co., ImageQuant LAS 500), the respective bands were detected by chemiluminescence. The detected bands were quantified by densitometry (GE Healthcare Co., ImageQuant TL v8.1.0.0). Inhibition rates were calculated from the intensities of the bands in the respective groups, with the luminescence of the band of the DMSO added group being 100%. The respective bands were corrected according to the intensity of the band corresponding to β-Actin.

Combinations of the primary antibodies and the secondary antibodies used in the present invention and their concentrations are as shown in Table 5.

TABLE 5

| | Primary antibody | Secondary antibody |
| --- | --- | --- |
| 1 | Anti-AXIN2 rabbit antibody (1/1000) | Anti-rabbit IgG goat antibody (1/5000) |
| 2 | Anti-c-MYC rabbit antibody (1/1000) | Anti-rabbit IgG goat antibody (1/5000) |
| 3 | Anti-β-Actin mouse antibody (1/10000) | Anti-mouse IgG goat antibody (1/5000) |

Figure 3:
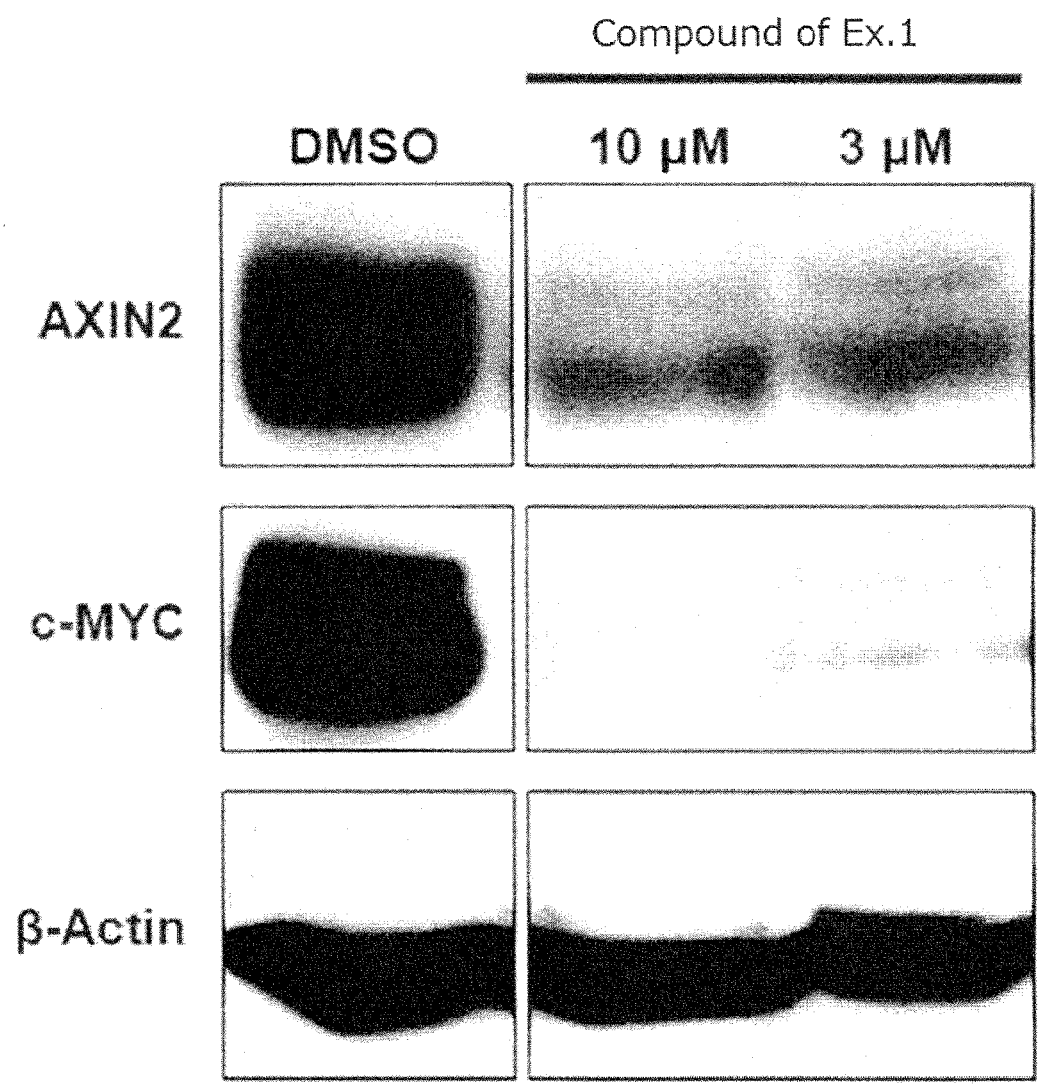
FIG. 3 shows that the compound of Example 1 inhibits AXIN2 and c-MYC protein expressions in HCT116 colorectal cancer cells in a concentration-dependent manner (Text Example 3).

As shown in FIG. 3 and Table 6, the compound of Example 1 inhibited the expressions of AXIN2 and c-MYC that are Wnt/β-catenin signaling target proteins in a concentration-dependent manner in HCT116 cells. From the above, inhibition of the activity of the Wnt/β-catenin-signaling pathway by the compound of the present invention was able to be confirmed at the expression levels of the target proteins.

TABLE 6

| | Inhibition rate (%) | |
| --- | --- | --- |
| | 10 μM | 3 μM |
| AXIN2 | 66.9 | 46.1 |
| c-MYC | 90.2 | 63.9 |

Test Example 4

Antitumor Effects in Mice Model Subcutaneously Transplanted with Human-Derived Cancer Cell Line The antitumor effects of the compound of the present invention were studied using nude mice subcutaneously transplanted with a human-derived colorectal cancer cell line HCT116, in which the Wnt signaling pathway was constantly activated.

(Preparation of Cancer-Bearing Model)

HCT116 cells cultured in the same manner as in Test Example 2 were adjusted with D-PBS (NACALAI TESQUE, INC.) so as to have a cell concentration of $7.5 \times 10^7$/mL, and the cell suspension was ice cooled in a 15 mL tube. To the cell suspension, Matrigel (BD Biosciences Co.) was added in an amount of one-fourth of the cell suspension to prepare a preparation for cell transplantation. Into the back of BALB/c Slc-nu/nu mice (female, 8 weeks old, Japan SLC, Inc.), 0.1 mL of the preparation for cell transplantation was subcutaneously injected. On the $7^{th}$ day after transplantation of the cancer cells, the mice were grouped so that average values of tumor volumes of the cancer-bearing mice were approximated (refer to the following calculation formulas).

(Preparation of Sample Solutions for Administration of Substance to be Tested)

Two sample solutions (8 mg/L and 4 mg/L) for administration of a substance to be tested were prepared in accordance with respective administration doses. The substance to be tested (512 mg) was dissolved in DMSO (6.4 mL, NACALAI TESQUE, INC.), and polyethylene glycol #400 (28.8 mL, NACALAI TESQUE, INC.) was added thereto to prepare a preservative solution for the substance to be tested. The preservative solution was stored in a light-shielding condition until the day of use. On the day of use, 5.5 mL of the preservative solution was transferred to a tube, and 4.5 mL of an aqueous solution of 30% (2-hydroxypropyl)-β-cyclodextrin (HP-β-CD) (Sigma-Aldrich Co. LLC.) was added thereto to prepare a 8 mg/mL sample solution for administration. This solution was diluted two-fold with a mixed solution of DMSO, polyethylene glycol #400 and the aqueous solution of 30% HP-β-CD (1:4.5:4.5) to prepare a 4 mg/L sample solution for administration.

(Tests of Antitumor Effects of Substance to be Tested)

To the respective mice transplanted with cancer cells (nine in each group), forced oral administration of doses of the substance to be tested calculated from their body weights was performed twice a day (at intervals of six hours or more) for 14 days in total. Tumor volumes of the respective mice were calculated using the following formulas, and the antitumor effects were evaluated using a relative tumor volume ratio as an indicator.

Tumor Volume = Major Axis × Minor Axis × Minor Axis/2

Tumor Volume Change = Tumor Volume On Each Measurement Day − Tumor Volume On The Day Of Starting Administration $$\text{Tumor Growth Inhibition Rate (TGI \%)} = \left(1 - \frac{\text{Average Value Of Tumor Volume Change In Each Administration Group}}{\text{Average Value Of Tumor Volume Change In Solvent Administration Group}}\right) \times 100$$

Figure 4:
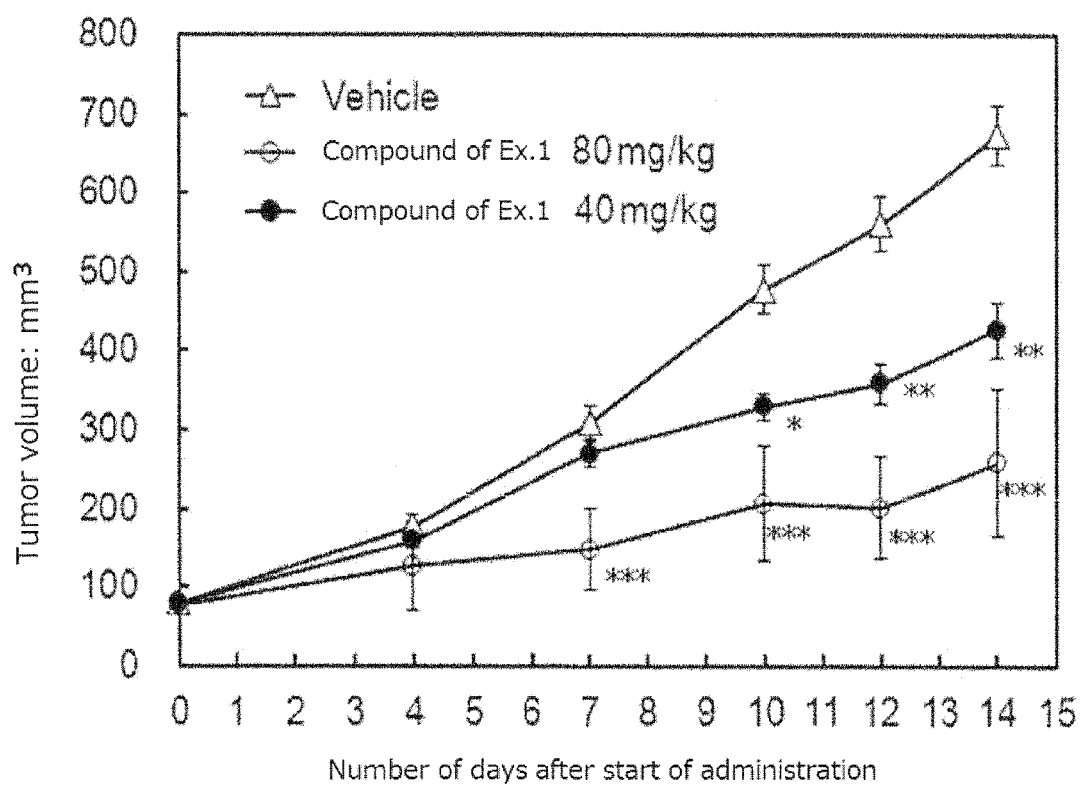
FIG. 4 shows that the compound of Example 1 inhibits tumor growth in a mouse model subcutaneously transplanted with a human-derived cancer cell line in a dose-dependent manner (Text Example 4).

As shown in FIG. 4, the compound of Example 1 that is the compound of the present invention showed significant tumor growth inhibition in a dose-dependent manner. Tumor growth inhibition rates (TGIs) (%) on the last administration day were 42% and 70% in 40 mg/kg and 80 mg/kg, respectively. This confirmed that the compound of the present invention inhibits the activity of the Wnt signaling pathway, and is useful in the treatment of cancer in which the Wnt signaling is constantly activated.

INDUSTRIAL APPLICABILITY

The compounds provided by the present invention are useful for treatment of diseases known to be associated with abnormal cell responses via the Wnt/β-catenin signaling pathway, in particular cancer. The compounds of the present invention are also useful for prevention of metastasis and recurrence of tumors by targeting cancer stem cells. Furthermore, the compounds of the present invention are useful for laboratory and researching reagents as Wnt/β-catenin signaling pathway inhibitors.

The invention claimed is:

1. A quinazoline derivative compound represented by the following formula (I):

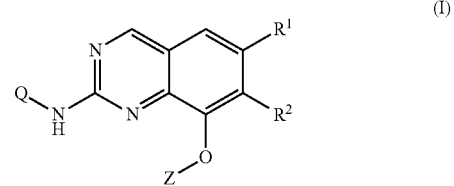

wherein $R^1$ and $R^2$ are a hydrogen atom, a halogen atom, or a C1-4 alkyl group; Z is a C3-7 cycloalkyl group having a substituent or a C5-7 cycloalkenyl group having a substituent; and Q is a bicyclic heteroaryl group formed by condensation of C4-6 membered ring optionally having a substituent, or a pharmaceutically acceptable salt thereof.

2. The quinazoline compound according to claim 1, wherein Z is a C3-7 cycloalkyl group having a substituent, or a pharmaceutically acceptable salt thereof.

3. The quinazoline compound according to claim 1, wherein Z is a hydroxycyclohexyl group, or a pharmaceutically acceptable salt thereof.

4. The quinazoline compound according to claim 1, wherein Z is a C3-7 cycloalkyl group having a substituent selected from the group consisting of a halogen atom, C1-4 alkyl group, C1-4 alkoxy group, amino group, C1-4 alkylamino group optionally substituted with a sulfonyl group, hydroxy group, carbamoyl group, carboxyl group, formyl group, acetyl group, mesyl group, benzoyl group and acylamino group; or a C5-7 cycloalkenyl group having a substituent selected from the group consisting of a halogen atom, C1-4 alkyl group, C1-4 alkoxy group, amino group, C1-4 alkylamino group optionally substituted with a sulfonyl group, hydroxy group, carbamoyl group, carboxyl group, formyl group, acetyl group, mesyl group, benzoyl group and acylamino group; and Q is a bicyclic heteroaryl group formed by condensation of C4-6 membered ring optionally having a substituent selected from the group consisting of a halogen atom, a C1C4 alkyl group optionally substituted with (a hydroxy group, a methoxy group or a pyrrolidinyl group), a C3-C5 cycloalkyl group, a C1-C4 alkoxy group, an amino group, a C1-C4 alkylamino group, a di(C1-C4 alkyl)amino group, a hydroxy group, a carbamoyl group, a carboxyl group, a morpholinyl group, a pyrrolidinyl group, a formyl group, an acetyl group, a mesyl group, a benzoyl group and an acylamino group;

or a pharmaceutically acceptable salt thereof.

5. The quinazoline compound according to claim 1, wherein Q is selected from the group consisting of a tetrahydroisoquinolyl group, a benzothiophenyl group, a benzimidazolyl group, a benzoxazolyl group, a benzothiazolyl group, an indolyl group, a benzotriazolyl group, a quinolyl group, an isoquinolyl group, a quinazolyl group and an indazolyl group, or a pharmaceutically acceptable salt thereof.

6. The quinazoline compound according to claim 2, wherein Q is selected from the group consisting of a tetrahydroisoquinolyl group, a benzothiophenyl group, a benzimidazolyl group, a benzoxazolyl group, a benzothiazolyl group, an indolyl group, a benzotriazolyl group, a quinolyl group, an isoquinolyl group, a quinazolyl group and an indazolyl group, or a pharmaceutically acceptable salt thereof.

7. The quinazoline compound according to claim 3, wherein Q is selected from the group consisting of a tetrahydroisoquinolyl group, a benzothiophenyl group, a benzimidazolyl group, a benzoxazolyl group, a benzothiazolyl group, an indolyl group, a benzotriazolyl group, a quinolyl group, an isoquinolyl group, a quinazolyl group and an indazolyl group, or a pharmaceutically acceptable salt thereof.

8. The quinazoline compound according to claim 4, wherein Q is selected from the group consisting of a tetrahydroisoquinolyl group, a benzothiophenyl group, a benzimidazolyl group, a benzoxazolyl group, a benzothiazolyl group, an indolyl group, a benzotriazolyl group, a quinolyl group, an isoquinolyl group, a quinazolyl group and an indazolyl group, or a pharmaceutically acceptable salt thereof.

9. A compound of cis-4-({2-[(1H-benzo[d]imidazol-6-yl)amino]quinazolyn-8-yl}oxy)cyclohexanol, or a pharmaceutically acceptable salt thereof.

* * * * *